(12) United States Patent
Romalis et al.

(10) Patent No.: US 7,145,333 B2
(45) Date of Patent: Dec. 5, 2006

(54) HIGH SENSITIVITY ATOMIC MAGNETOMETER AND METHODS FOR USING SAME

(75) Inventors: Michael Romalis, Princeton, NJ (US); Tom Kornack, Princeton Junction, NJ (US); Joel Allred, Seattle, WA (US); Rob Lyman, Charlottesville, VA (US)

(73) Assignees: The Trustees of Princeton University, Princeton, NJ (US); University of Washington, Seattle, WA (US)

( * ) Notice: Subject to any disclaimer, the term of this patent is extended or adjusted under 35 U.S.C. 154(b) by 0 days.

(21) Appl. No.: 11/135,853

(22) Filed: May 23, 2005

(65) Prior Publication Data

US 2005/0206377 A1    Sep. 22, 2005

Related U.S. Application Data

(63) Continuation of application No. 10/687,012, filed on Oct. 16, 2003, now Pat. No. 7,038,450.

(60) Provisional application No. 60/418,696, filed on Oct. 16, 2002.

(51) Int. Cl.
*G01V 3/00* (2006.01)
(52) U.S. Cl. .................... 324/304; 324/301
(58) Field of Classification Search ............... 324/304, 324/301, 300, 318, 322
See application file for complete search history.

(56) References Cited

U.S. PATENT DOCUMENTS

| | | | |
|---|---|---|---|
| 4,005,355 A | | 1/1977 | Hopper et al. |
| 4,525,672 A | * | 6/1985 | Lam et al. .................. 324/304 |
| 4,617,462 A | * | 10/1986 | Holt ........................... 250/251 |
| 5,189,368 A | * | 2/1993 | Chase ......................... 324/304 |
| 6,472,869 B1 | | 10/2002 | Upschulte et al. |
| 7,038,450 B1 | | 5/2006 | Romalis et al. |

OTHER PUBLICATIONS

SQUID Sensors: Fundamentals, Fabrication and Applications, Ed. Weinstock, H., Kluwer Academic (1996).
Affolderbach, C., et al., An All-Optical, High Sensitivity Magnetic Gradiometer, Appl. Phys. (2002) B 75:605-612.
Alexandrov, E.B., et al., Double-Resonance Atomic Magnetometers: from Gas Discharge to Laser Pumping, Laser Phys. (1996) 6:244-251.
Aleksandrov, E.B., et al., Laser Pumping in the Scheme of an Mx-Magnetometer, Optics and Spectr. (1995) 78:292-298.

(Continued)

*Primary Examiner*—Louis M. Arana
(74) *Attorney, Agent, or Firm*—McCarter & English, LLP

(57) ABSTRACT

The present invention provides a high sensitivity atomic magnetometer and methods of measuring low intensity magnetic fields that relate to the use of an alkali metal vapor and a buffer gas; increasing the magnetic polarization of the alkali metal vapor thereby increasing the sensitivity of the alkali metal vapor to a low intensity magnetic field; probing the magnetic polarization of the alkali metal vapor, the probing means providing an output from the alkali metal vapor, the output including characteristics related to the low intensity magnetic field; and measuring means that receives the output, determines the characteristics of the low intensity magnetic field, and provides a representation of the low intensity magnetic field. In addition, the invention relates to a magnetometer and methods that provide a representation of a first magnetic field originating within a sample volume. The sample volume may be part or all of a subject, such as a human subject. The representation includes a representation of a source of a magnetic field occurring within the sample volume displayed in one, two, or three of three orthogonal Cartesian coordinates, referenced to the sample volume.

73 Claims, 12 Drawing Sheets

OTHER PUBLICATIONS

Allred, J.C., et al., High Sensitivity Atomic Magnetometer Unaffected by Spin-Exchange Relaxation, Phys. Rev. Lett. (2002) 89:130801-1-130801-4.

Bison, G., et al., A Laser-Pumped Magnetometer for the Mapping of Human Cardiomagnetic Fields, Appl. Phys. B. (2003) 76:325-328.

Bison, G., et al., Dynamical Mapping of the Human Cardiomagnetic Field with a Room-Temperature, Laser-Optical Sensor, Opt. Expr. (2003) 11:904-909.

Budker, D., et al., Resonant Nonlinear Magneto-Optical Effects in Atoms, Rev. Mod. Phys. (2002) 74:1153-1201.

Budker, D., et al., Nonlinear Magneto-Optic Effects with Ultranarrow Widths, Phys. Rev. Lett. (1998) 81:5788-5791.

Budker, D., et al., Sensitive Magnetometry Based on Non-linear Magneto-optical Rotation, Phys. Rev. A (2000) 62:043403-1-043403-7.

Clem, T.R., Superconducting Magnetic Gradiometers for Underwater Target Detection, Nav. Eng. J. (1998) 110:139-149.

Del Gratta C., et al. Magnetoencephalography—a Noninvasive Brain Imaging Method with 1 ms Time Resolution, Rep. Prog. Phys. (2001) 64:1759-1814.

Drung, D., et al., Improved Direct-Coupled dc SQUID Read-Out Electronics with Automatic Bias Voltage Tuning, IEEE T. Appl. Supercon. (2001) 11:880-883.

Greenberg, Ya.S., Application of Superconducting Quantum Interference Devices to the Nuclear Magnetic Resonance, Rev. Mod. Phys. (1998) 70:175-222.

Hämäläinen, M., et al., Magnetoencephalography—Theory Instrumentation and Applications to Non-Invasive Studies of the Working Human Brain, Rev. Mod. Phys. (1993) 65:413-497.

Happer, W., Optical Pumping, Rev. Mod. Phys. (1972) 44:169-249.

Happer, W., et al., Effect of Rapid-Spin-Exchange on the Magnetic-Resonance Spectrum of Alkali Vapors, Phys. Rev. A (1977) 16:1877-1991.

Happer, W., et al., Spin-Exchange Shift and Narrowing of Magnetic Resonance Lines in Optically Pumped Alkali Vapors, Phys. Rev. Lett. (1973) 31:273-276.

Harry, G.M., et al., Two-Stage Superconducting-Quantum-Interference-Device Amplifier in a High-Q Gravitational Wave Transducer, Appl. Phys. Lett. (2000) 76:1446-1448.

Kelha, V.O., et al., Design, Construction and Performance of a Large-Volume Magnetic Shield, IEEE Trans. Magn. (1982) 18:260-270.

Kirschvink, J.L., et al., Paleomagnetic Evidence of a Low-Temperature Origin of Carbonate in the Martian Meteorite ALH84001, Science (1997) 275:1629-1633.

Kominis, I.K., et al., A Subfemtotesla Multichannel Atomic Magnetometer, Nature (2003) 422:596-599.

McDermott, R, et al., Liquid-State NMR and Scalar Couplings in Microtesla Magnetic Magnetic Fields, Science (2002) 295:2247-2249.

Murthy, S.A., et al., New Limits on the Electron Electric Dipole Moment from Cesium, Phys. Rev. Lett. (1989) 63:965-968.

Nenonen, J., et al., Thermal Noise in Biomagnetic Measurements, Rev. Sci. Instr. (1996) 67:2397-2405.

Nenonen, J., et al., Thermal Noise in a Magnetically Shielded Room, in Biomagnetism '87, Ed. K. Atsumi, et al. Denki University Press, Tokyo, (1988), p. 426-429.

Oukhanski, N., et al., Low-Drift Broadband Directly Coupled dc SQUID Read-Out Electronics, Physica C (2002) 268:166-170.

Rodriquez, E., et al., Perception's Shadow: Long-Distance Synchronization of Human Brain Activity, Nature (1999) 397:430-433.

Tralshawala, N., et al., Practical SQUID Instrument for Non-Destructive Testing, Appl. Phys. Lett. (1997) 71:1573-1575.

Ts'o. D.Y., et al., Functional Organisation of Primate Visual Cortex Revealed by High-Resolution Optical Imaging, Science (1990) 249:417-420.

Tsuei, C.C., et al., Phase Sensitive Evidence for d-Wave Pairing Symmetry in Electron-Doped Cuprate Superconductors, Phys. Rev. Lett. (2000) 85:182-185.

Varpula, T., et al., J. Appl. Phys. (1984) 55:4015-4021.

Zimmerman, J.E., et al., Design and Operation of Stable RF-Biased Superconducting Point-Contact Quantum Devices, and a note on Properties of Perfectly Clean Metal Contacts., J. Appl. Phys. (1970) 41:1572-1580.

* cited by examiner

HIGH SENSITIVITY ATOMIC MAGNETOMETER AND METHODS FOR USING SAME

RELATED APPLICATION

This application claims the benefit of priority of provisional application U.S. Ser. No. 60/418,696, filed Oct. 16, 2002.

GOVERNMENT RIGHTS

The present invention was made with Government support and the Government has certain rights in the invention.

FIELD OF THE INVENTION

The present invention relates to a highly sensitive magnetometer having the ability to detect very low magnetic field intensities, and to methods of measuring such low intensity magnetic fields. More particularly, the invention relates to atomic magnetometers that rely on polarizing alkali metal vapor, and probing the state of magnetization of the polarized metal atoms. The invention further relates to measuring characteristics of a magnetic field originating from a variety of sources, including organs of the human body.

BACKGROUND OF THE INVENTION

Over the past several decades ultra-sensitive magnetometers have found a wide range of applications, from condensed matter experiments (Tsuei, C. C. et al., *Phys. Rev. Lett.* 85, 182–185 (2000)) and gravitational wave detection (Harry, G. M. et al., *Appl. Phys. Lett.* 76, 1446–1448 (2000)), to detection of nuclear magnetic resonance (NMR) signals (Greenberg, Ya. S., *Rev. Mod. Phys.* 70, 175–222 (1998); McDermott, R. et al., *Science* 295, 2247–2249 (2002)), studies of paleomagnetism (Kirschvink, J. L. et al., *Science* 275, 1629–1633 (1997)), non-destructive testing (Tralshawala, N. et al., *Appl. Phys. Lett.* 71, 1573–1575 (1997)), and ordinance detection (Clem, T. R., *Nav. Eng. J* 110, 139–149 (1998)). For the last 30 years superconducting quantum interference devices (SQUIDs) operating at 4K have been unchallenged as ultra-high-sensitivity magnetic field detectors (*SQUID Sensors: Fundamentals, Fabrication and Applications*, Ed. Weinstock, H., Kluwer Academic (1996)) with a sensitivity reaching down to 1 $fT/Hz^{12}$ (where fT designates femtotesla, or $10^{-15}$ tesla).

The most notable application of magnetic field sensors has emerged in the measurement of biomagnetism (Hämäläinen M. et al., *Rev. Mod. Phys.* 65, 413–497 (1993); Rodriguez, E. et al., *Nature* 397, 430–433 (1999)), i.e. the detection of the weak magnetic fields produced by the human brain, heart, and other organs. These instruments have enabled, among other applications, mapping of the magnetic fields produced by the brain and localization of the underlying electrical activity (magnetoencephalography, MEG). For example, measurements of the magnetic field produced by the brain have been used to diagnose epilepsy and to study neural responses to auditory and visual stimuli. Low temperature SQUID sensors (Zimmerman, J. E. et al., *J. Appl. Phys.* 41, 1572–1580 (1970); Drung, D. et al., *IEEE T. Appl. Supercon.* 11, 880–883 (2001); Oukhanski, N. et al., *Physica C* 368, 166–170 (2002)), which so far have dominated all of the aforementioned applications, have attained sensitivity levels of 0.9–1.4 $fT/Hz^{1/2}$ with a pick-up coil area on the order of 1 $cm^2$. Their noise in the low-frequency range of interest for biomagnetic studies (<100 Hz), however, is typically somewhat higher; indeed, commercial SQUID magnetometers typically (Del Gratta C, et al., *Rep. Prog. Phys.* 64, 1759–1814 (2001)) have noise levels of about 5 $fT/Hz^{1/2}$, partly due to magnetic noise generated by electrically-conductive radiation shielding of their liquid helium dewars (Nenonen, J. et al., *Rev. Sci. Instr.* 67, 2397–2405 (1996)).

Atomic magnetometers, an important alternative to SQUID instruments, are based on detection of Larmor spin precession of optically pumped atoms. Alkali metal magnetometers have approached similar levels of sensitivity when using large measurement volumes (Aleksandrov, E. B. et al., *Optics and Spectr.* 78, 292–298 (1995); Budker, D. et al., *Phys. Rev. A* 62, 043403 (2000)), but have much lower sensitivity in more compact designs suitable for magnetic imaging applications (Affolderbach, C. et al., *Appl Phys B* 75, 605–612 (2002)).

Spin exchange in alkali metal vapors has been discussed in Happer W. et al. (Phys. Rev. Lett. 31, 273 (1973) and in Happer W. et al. (Phys. Rev. A 16 1877 (1977)), which report experimental and theoretical aspects of observing magnetic resonance in high density alkali metal vapors in the presence of a buffer gas. U.S. Pat. No. 4,005,355 to Happer. et al. discloses a high-density alkali vapor optically pumped to produce a narrow magnetic resonance line with a frequency proportional to a magnetic field.

Bison et al. (a) (Appl. Phys. B. 76, 325 (2003) and Bison et al. (b) (Opt. Expr. 11, 908 (2003)) disclose an optically pumped cesium atom magnetometer for use in dynamic cardiac magnetic imaging. Observed magnetic noise levels in Bison et al. (b) appear to be on the order of 1000 $fT/Hz^{1/2}$.

Upschulte et al. (U.S. Pat. No. 6,472,869) discloses a diode laser-pumped alkali magnetometer. In Upschulte et al., response radiation includes photons that indicate one unit of angular momentum indicative of the torque due to the magnetic field, and a photodiode and scope that act as a means for measuring the response radiation. Upschulte et al. disclose a projected sensitivity of less than 6 $pT/Hz^{1/2}$ (pT=picotesla or $10^{-12}$ tesla).

In view of the disadvantages of relatively poor sensitivity, and drawbacks such as large bulk and use of cryogenic systems summarized above, there remains a need for a magnetometer that can operate in the absence of expensive liquid helium dewars needed to maintain superconducting conditions, and also to avoid the need for other liquefied gas dewars used with higher temperature superconducting devices. In addition there remains a need for the development of advantageous atomic magnetometers with high sensitivity. There further is a need for a compact magnetometer that is relatively inexpensive to assemble and operate. Additionally there is a need for carrying out biomagnetic measurements with high spatial resolution in order to observe localized areas within a living subject. The present invention addresses these and related unmet needs.

SUMMARY OF THE INVENTION

In a first aspect, the present invention provides a high sensitivity atomic magnetometer that includes
  a) a sensing cell containing a mixture including an alkali metal vapor and a buffer gas, wherein the sensing cell is exposed to a background magnetic field lower than a first predetermined value;

b) means for increasing the magnetic polarization of the alkali metal vapor thereby increasing the sensitivity of the alkali metal vapor to a low intensity magnetic field;

c) magnetizing means for imposing a magnetic field on a volume of space including the sensing cell;

d) means for probing the magnetic polarization of the alkali metal vapor, the probing means providing an output from the alkali metal vapor, the output including characteristics related to the low intensity magnetic field; and e) measuring means wherein the measuring means receives the output, determines the characteristics of the low intensity magnetic field, and provides a representation of the low intensity magnetic field;

wherein the limit of detectability of the atomic magnetometer is lower than a second predetermined value.

In an additional aspect, the present invention provides a high sensitivity atomic magnetometer that generates a representation of a first magnetic field originating within a sample volume, the magnetometer including a) a sensing cell sensitive to low intensity magnetic fields including an alkali metal vapor and a buffer gas, the sensing cell being adjacent to a sample volume including a component generating a first magnetic field, wherein the sensing cell is exposed to a background magnetic field lower than a first predetermined value;

b) means for increasing the magnetic polarization of the alkali metal vapor, wherein the magnetic polarization of the alkali metal vapor includes a contribution from the first magnetic field;

c) magnetizing means for imposing a magnetic field on a volume of space including the sensing cell;

d) means for probing the magnetic polarization of the alkali metal vapor, the probing means providing an output from the vapor including characteristics related to the first magnetic field; and e) measuring means for receiving the output, determining the characteristics of the first magnetic field, and providing a representation of the first magnetic field;

wherein the limit of detectability of the atomic magnetometer is lower than a second predetermined value.

In yet an additional aspect, the present invention provides a method for providing a representation of a low intensity magnetic field detected by a sensing cell that has high sensitivity to a magnetic field, the method including the steps of:

a) providing an atomic magnetometer such as described above;

b) increasing the magnetic polarization of the alkali metal vapor, thereby increasing the sensitivity of the alkali metal vapor to a low intensity magnetic field;

c) reorienting the magnetic polarization of the alkali metal vapor using a magnetic field;

d) probing the magnetic polarization of the reoriented alkali metal vapor with the probing means, wherein the probing means provides an output whose characteristics are related to the low intensity magnetic field; and e) receiving the output in the measuring means, determining the characteristics of the low intensity magnetic field, and providing a representation of the low intensity magnetic field detected by the sensing cell.

In still a further aspect, the present invention provides a method for providing a representation of a first magnetic field originating within a sample volume, the method including the steps of:

a) providing a high sensitivity apparatus described described in the preceding;

b) identifying a sample volume adjacent to the sensing cell;

c) increasing the magnetic polarization of the alkali metal vapor, wherein the magnetic polarization of the alkali metal vapor includes a contribution from the first magnetic field;

d) reorienting the magnetic polarization of the alkali metal vapor using a magnetic field;

e) probing the magnetic polarization of the reoriented alkali metal vapor with the probing means, wherein the probing means provides an output whose characteristics are related to the first magnetic field; and f) receiving the output in the measuring means, wherein the measuring means determines the characteristics of the first magnetic field and provides a representation of the first magnetic field detected by the sensing cell.

In important embodiments of the atomic magnetometer methods disclosed herein, the magnetometer includes magnetic shielding enclosing a region of space that includes the magnetizing means, the sample volume, and the sensing cell. The shielding and the magnetizing means contribute to providing that the first predetermined value is $10^{-8}$ tesla or lower.

In significant embodiments of the atomic magnetometer and methods of the invention, the density of the alkali metal in the vapor is about $10^{11}$ cm$^{-3}$ or greater. The alkali metal is chosen from among sodium, potassium, rubidium and cesium, and, in still more significant embodiments, the alkali metal is potassium. Importantly, the sensing cell is maintained at a temperature that is effective to provide an alkali metal vapor at a density greater than about $10^{11}$ cm$^{-3}$.

In advantageous embodiments of atomic magnetometer and methods disclosed herein, the buffer gas includes a noble gas. The buffer gas may include one or more isotopes of helium, and is included at a pressure in the range from about 1 atm to about 10 atm. Significantly, the buffer gas may further include nitrogen gas, or it may be constituted solely of nitrogen gas.

Factors such as the temperature and consequent density of the vapor, and the presence and composition of the buffer gas contribute to providing that the second predetermined value describing the sensitivity limit of the present magnetometer is about 1 femtotesla $(Hz)^{-1/2}$, or even lower.

In still further significant embodiments of the atomic magnetometer and methods disclosed herein, the sensing cell transmits a plurality of beams of radiation through the alkali metal vapor, wherein at least two of the beams are physically resolved from each other. In addition, the volume of the sensing cell advantageously is less than about 200 cm$^3$.

In yet a further important embodiment of the atomic magnetometer and methods, the means for increasing the magnetic polarization of the alkali metal vapor includes a first radiation generating means that generates a first beam of radiation illuminating the alkali metal vapor. The first beam is effective to increase the magnetic polarization of the alkali metal vapor. In still more important embodiments, the first radiation generating means includes a first laser device. In another important embodiment, the first radiation generating means further includes a first optical polarizing means that polarizes the first beam of radiation. The first optical polarizing means may impose linear polarization on the first beam of radiation, or, alternatively, it may impose circular polarization on the first beam of radiation.

In yet a further important embodiment, the first radiation generating means further includes a first modulator that modulates the first beam of radiation by a first modulation function.

Still additional significant embodiments of the atomic magnetometer and methods of the present invention provide that the probing means includes one or more second radiation generating means that generates one or more second beams of radiation traversing the alkali metal vapor; after the one or more second beams traverse the vapor they constitute the output of the magnetometer. In still more significant embodiments the second radiation generating means includes a second laser device. Still more significantly, the second radiation generating means includes a second optical polarizing means that polarizes the second beam of radiation. The second optical polarizing means may impose linear polarization on the second beam of radiation, or it may impose circular polarization on the second beam of radiation. Still additionally, in significant embodiments the second radiation generating means includes a second modulator that modulates the second beam of radiation by a second modulation function.

Still further important embodiments of the atomic magnetometer and methods of the present invention provide that the magnetizing means provides a probing magnetic field in one, two, or all three of the orthogonal directions, x, y, and/or z. In addition, the magnetizing means provides a probing magnetic field modulated by a third modulation function.

In yet additional advantageous embodiments of the atomic magnetometer and methods of the present invention, the measuring means includes one or more output detecting means that provides one or more signals. The one or more signals contain characteristics related to the low intensity magnetic field. The measuring means also includes one or more signal processing means for receiving the one or more signals and providing the representation. Still more advantageously the output detecting means includes radiation detecting means that detects a second beam of radiation output from the alkali metal vapor. In particular advantageous embodiments, a third optical polarizing means is situated between the sensing cell and the radiation detecting means. The third optical polarizing means may include a linear polarization analyzer, or it may include a circular polarization analyzer.

In still additional advantageous embodiments the radiation detecting means includes one or more photodetectors, such that each photodetector provides a signal that contains characteristics related to the low intensity magnetic field. When a first modulation function or second modulation function has been employed, the signal advantageously includes a component modulated by the first modulation function or the second modulation function, or both.

In still additional advantageous embodiments of the atomic magnetometer and methods of the invention, the signal processing means receives at least a portion of a signal from the output detecting means. The signal processing means operates to resolve characteristics related to the low intensity magnetic field from the signal and provides a representation thereof, such that the representation characterizes the low intensity magnetic field detected by the sensing cell. When the signal is modulated by a first modulation function or a second modulation function, or both, the signal processing means detects a component in the signal that is modulated by the first modulation function or the second modulation function, or both.

In still additional highly advantageous embodiments of the invention, the measuring means includes two or more output detecting means, wherein a first output detecting means detects radiation traversing a first region of the alkali metal vapor and a second output detecting means detects radiation traversing a second, different, region of the alkali metal vapor. In these embodiments the first output detecting means provides a signal to a first signal processing means and the second output detecting means provides a signal to a second signal processing means; the first signal processing means provides a representation of the low intensity magnetic field-sensed in the first region and the second signal processing means provides a representation of the low intensity magnetic field sensed in the second region.

In still additional advantageous embodiments, the distance separating a first region and a second region is about 1 cm or less, and the volume of such a region is about 1 cm$^3$ or less.

In still additional important embodiments of the invention, a sample volume defined in a magnetometer and method includes at least a portion of a mammalian subject.

In yet a further important embodiment of the magnetometer and methods of the invention, the representation includes a representation of a source of a first magnetic field occurring within the sample volume displayed in one of three orthogonal Cartesian coordinates, or in two of three orthogonal Cartesian coordinates, or in three of three orthogonal Cartesian coordinates, referenced to the sample volume.

DETAILED DESCRIPTION OF THE INVENTION

Figure 1:
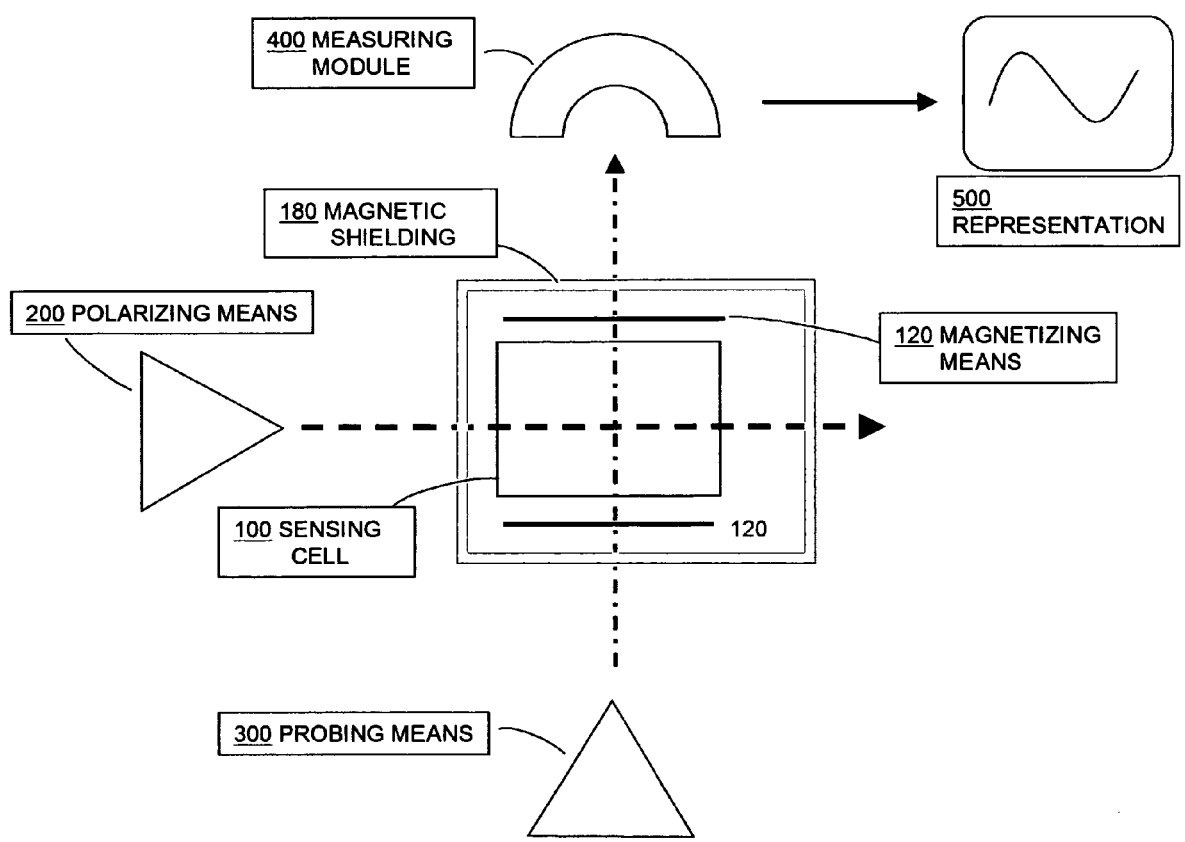
FIG. 1. Schematic diagram of several components employed in an embodiment of an atomic magnetometer of the invention.

As used herein, the term "magnetic polarization", and similar terms and phrases, relate to the spin polarization of an ensemble of atoms having a nonzero quantum number, such as a nonzero orbital angular momentum quantum number, or a nonzero electron spin quantum number, or a nonzero nuclear spin quantum number, or any combination thereof. An ensemble having nonzero spin responds to a magnetic field. Furthermore, the state of polarization is changed in response to changes in the magnetic field imposed on the ensemble.

As used herein the term "characteristics" and similar terms and phrases are used to relate a) to a source of a magnetic field; b) to the properties of such a magnetic field in a region of space in which other sources of magnetization are also present; c) to the magnetic polarization of an ensemble of atoms sensitive to magnetic field originating from the source even when other sources of magnetization are also present; d) to the altered properties of a probing modality wherein the alteration reflects the effects of the magnetization sensed by the ensemble of atoms and including the effects of the magnetic field originating from the source; e) to the properties of a signal generated by such an altered probing modality wherein the signal includes the effects of the magnetization sensed by the ensemble of atoms and including the effects of the magnetic field originating from the source; and f) to a representation of the magnetic signal originating from the source after the effects of all other sources of magnetization have been removed or minimized. Characteristics include properties relating to the magnetic field originating from the source including, by way of nonlimiting example, spatial, temporal, amplitudinal, vectorial and similar properties of a source magnetic field. Thus the phrase "characteristics related to a magnetic field" and similar phrases, as used herein, is intended to convey that characteristics of a source of a magnetic field, the properties of a magnetic field, the magnetic polarization of atoms, or characteristics of a probing modality, or characteristics of a signal, or characteristics of a representation, include information related to properties such as those exemplified above.

As used herein, the term "output" and similar terms or phrases relate to a probe modality that has traversed a sensing cell of the invention and whose properties have been altered by traversing the alkali metal vapor contained in the cell. The output probe modality, for example an output beam of probe radiation, includes characteristics of the magnetic polarization of the alkali metal vapor.

As used herein, the term "representation", and similar terms and phrases, relate to any verbal, numerical, tabular, graphical or multidimensional display conveying information about, especially characteristics related to, a measured magnetic field strength provided by the atomic magnetometer of the invention. Thus, a representation may be as elementary as a single number or a verbal equivalent of such a number. Alternatively, a representation may be a set of numbers describing different aspects of the information related to the measured magnetic field strength. Such a set of numbers may be displayed, by way of nonlimiting example, as a vector, or as a matrix, or as a table. A representation may further include a graphical display providing a visual or pictorial image of the results of measurements of the magnetic field strength provided by the atomic magnetometer of the invention. In yet another example of a representation, additional dimensions portraying one, two, or three-dimensional spatial images, as well as yet a different additional dimension representing time may be included in a representation. Any equivalent means of representing the results of the measurements of magnetic field strength provided by the atomic magnetometer of the invention is understood to be within the scope of the term "representation".

As used herein, the term "noble gas" and similar terms and expressions relates to any isotope of helium, neon, argon, krypton, xenon or radon. In addition, any mixture of noble gases is included by usage of "noble gas".

As used herein the term "optical polarization" and similar terms and phrases used that relate specifically to optical radiation are distinguished from "magnetic polarization" and similar terms. "Optical polarization" relates to the state of polarization of the wave aspect of radiation as it propagates. Optical polarization may synonymously be characterized as linearly polarized or plane polarized, wherein a wave describing the radiation is thought to vibrate in a single plane. Optical polarization characterized as circularly polarized relates to vibration of a wave of radiation that describes a helix as it propagates; the projection of the helix on to a plane perpendicular to the direction of propagation describes a circle. The helix may have a left handed sense of rotation as it propagates or it may have a right handed sense of rotation.

The present invention provides an atomic magnetometer of compact size and high sensitivity. The invention additionally provides methods of determining magnetic field strengths, their time dependence, and their spatial distribution with convenience, versatility and great sensitivity. Because of these and other attributes described herein, the invention provides distinct advantages with respect to atomic magnetometers already available in the field.

An important attribute of the magnetometer is that the magnetic field sensing substance, an alkali metal vapor, is used at relatively high number density. This has the beneficial effect of increasing the concentration of sensing atoms present per unit volume. Without wishing to be bound by theory, there may be a concern that high atom density may lead to disadvantageous increase in collisional spin exchange rates among the alkali metal atoms. In order to overcome the possibility that such a detriment may arise, the inventors operate the magnetometer in a small magnetic field. Without wishing to be bound by theory, it is believed that operating the magnetometer in a small magnetic field and with high number density of alkali metal eliminates spin-exchange relaxation. Furthermore, it is believed that the rate of response of the spins to the magnetic field, the gyromagnetic ratio, is changing with the degree of spin polarization. Thus, operating near zero magnetic field eliminates the sensitivity of the magnetometer to variations of the spin polarization across the sample.

Additionally, the inventors introduce a buffer gas, such as a noble gas, that slows the rate at which the atoms hit the wall. In addition nitrogen gas at a moderate partial pressure is also included to quench the optical transitions. Certain combinations of alkali metal-noble gas mixtures offer more advantageous slowing of collision spin relaxation than others. Additionally, the buffer gas slows diffusion of the alkali metal atoms, allowing independent measurement of the magnetic field in several adjacent regions of the cell. In addition, the buffer gas broadens the optical resonance lines of the atoms, allowing one to use low-cost broadband lasers and eliminating the need for precise stabilization of the laser frequency.

An additional advantageous property of the present magnetometer is that, as a consequence of its increased sensitivity, the overall dimensions of a cell containing the alkali metal vapor mixture is considerably reduced. This has the advantage of conferring convenience, greater portability, and greater versatility in obtaining measurements on various subjects or objects.

The present invention provides a high sensitivity atomic magnetometer that includes several important components (see FIG. 1). A sensing cell 100 is an enclosure containing a mixture that becomes magnetically sensitive upon operation of the apparatus. The sensing cell contains a mixture of an alkali metal vapor that is sensitive to a low intensity magnetic field, a buffer gas, and may additionally contain a quenching gas component. The alkali metal vapor is provided from a reservoir of the metal introduced as a solid upon fabrication of the cell. The sensitivity of the magnetometer is advantageously enhanced by operation at a high density of the alkali metal; this is achieved by heating the sensing cell to a temperature that provides a relatively high partial pressure of the alkali metal in the vapor. In various embodiments, the number density of the alkali metal atoms in the vapor may about $10^{11}$ cm$^{-3}$ or greater, or about $10^{12}$ cm$^{-3}$ or greater, or about $10^{13}$ cm$^{-3}$ or greater, or about $5\times10^{13}$ cm$^{-3}$ or greater, or about $10^{14}$ cm$^{-3}$ or greater, or about $5\times10^{14}$ cm$^{-3}$ or even greater. In important embodiments of a magnetometer of the invention, the alkali metal density is sufficiently high that the maximum deviation of the magnetic field from zero times $\mu/h$, where $\mu$ is the magnetic dipole moment, and $h$ is Planck's constant, is much less than the spin exchange rate. In addition, the sensing cell is maintained in an environment that is free of background magnetic fields; the background magnetic field is lower than a predetermined value. The background may be less than about $10^{-7}$ tesla, or less than about $3\times10^{-8}$ tesla, or less than about $10^{-8}$ tesla, or less than about $3\times10^{-9}$ tesla, or even less. An important way of achieving this is to apply bias fields using the magnetizing means 120 (FIG. 1; described more fully below) to counter any residual environmental fields reaching the sensing cell. For example, a feedback system may be utilized to keep the magnetic field close to zero, such as a feedback using a signal generated by an output detecting means (described more fully below).

In order to provide such high vapor densities of the alkali metal the sensing cell is maintained at an elevated temperature effective to provide an alkali metal vapor. In various embodiments the alkali metal may be chosen from among sodium, potassium, rubidium and cesium; in a particularly significant embodiment the alkali metal is potassium.

The sensing cell employed in the atomic magnetometer also contains a buffer gas. Components of the buffer gas are chemically unreactive with the alkali metal atoms in the vapor. In common embodiments of the invention the buffer gas includes a noble gas, such as helium, neon, argon, xenon or krypton; in a significant embodiment of the invention, the buffer gas contains one or more isotopes of helium, i.e., $^3$He or $^4$He. The buffer gas is included at a relatively high pressure. It is believed that a relatively high pressure of the buffer gas has the beneficial effects of shortening the diffusion path of the alkali metal, thereby enhancing the spatial resolution of the magnetometer. Advantageously, the pressure of the buffer gas may be about 1 atm or greater, or 2 atm or greater, or 3 atm or greater, or 5 atm or greater, or 8 atm or greater, or even 10 atm or greater. In addition, the buffer gas may also include a quenching component; in favorable embodiments the quenching component may be nitrogen gas. When present, the nitrogen gas may be included at a partial pressure of about 10 torr or greater, or about 30 torr or greater, or about 60 torr or greater, or about 100 torr or greater, or even about 200 torr or greater. Furthermore, the buffer gas may be constituted solely of nitrogen gas, in which case its pressure may range as high as 10 atm. In general, the pressure of the buffer gas is sufficient to slow the diffusion of the alkali metal atoms to the walls of the sensing cell, thus achieving long spin relaxation time. Any equivalent buffer gas is contemplated to be within the scope of the invention.

The sensing cell may be fabricated of any material compatible with the requirements of the apparatus; for example, the material must be inert with respect to the reactive alkali metal vapor, and must sustain the physical stress of high pressure of the buffer gas. As will be seen below, in many embodiments of the magnetometer the sensing cell transmits optical radiation through it; thus the sensing cell must be transparent to the radiation used and have windows that transmit beams of radiation without loss or distortion. In addition the sensing cell must be maintained at elevated temperature to volatilize the alkali metal atoms. The sensitivity of the magnetometer is related to the number of magnetic field sensing atoms employed. Thus, in addition to increasing the number density of alkali metal atoms by raising the temperature, their number may also be increased by employing a larger sensing cell. This advantage is offset by the desire of the present inventors to keep the overall dimensions of the magnetometer as compact as possible. As employed in the present invention, the enclosed volume of the sensing cell may be about 300 cm$^3$ or less, or about 200 cm$^3$ or less, or about 100 cm$^3$ or less, or about 75 cm$^3$ or less, or about 50 cm$^3$ or less, or about 25 cm$^3$ or less, or about 10 cm$^3$ or less, or about 5 cm$^3$ or less.

A further important module of the magnetometer disclosed herein includes means for increasing the magnetic polarization of the alkali metal vapor contained in the sensing cell (FIG. 1, 200). This serves to increase the sensitivity of the alkali metal vapor to a low intensity magnetic field impinging upon the sensing cell 100. In general, magnetic polarization in the alkali metal vapor may be increased by transmitting into the vapor any form of energy that includes a strong magnetic component. The present invention contemplates any means for transmitting such magnetic energy into the sensing cell, including, by way of nonlimiting example, electromagnetic radiation, focused or oriented magnetic fields, and any equivalent means that effectively increases the magnetic polarization of the alkali metal atoms. The heavy dashed line projecting from the means for increasing the magnetic polarization of the alkali metal vapor, 200, to and, in general through, the sensing cell 100 portrayed in FIG. 1 is intended to indicate that the means 200, although separate from the sensing cell 100, nevertheless projects the energy for increasing the magnetic polarization of the alkali metal vapor into the vapor.

Figure 2:
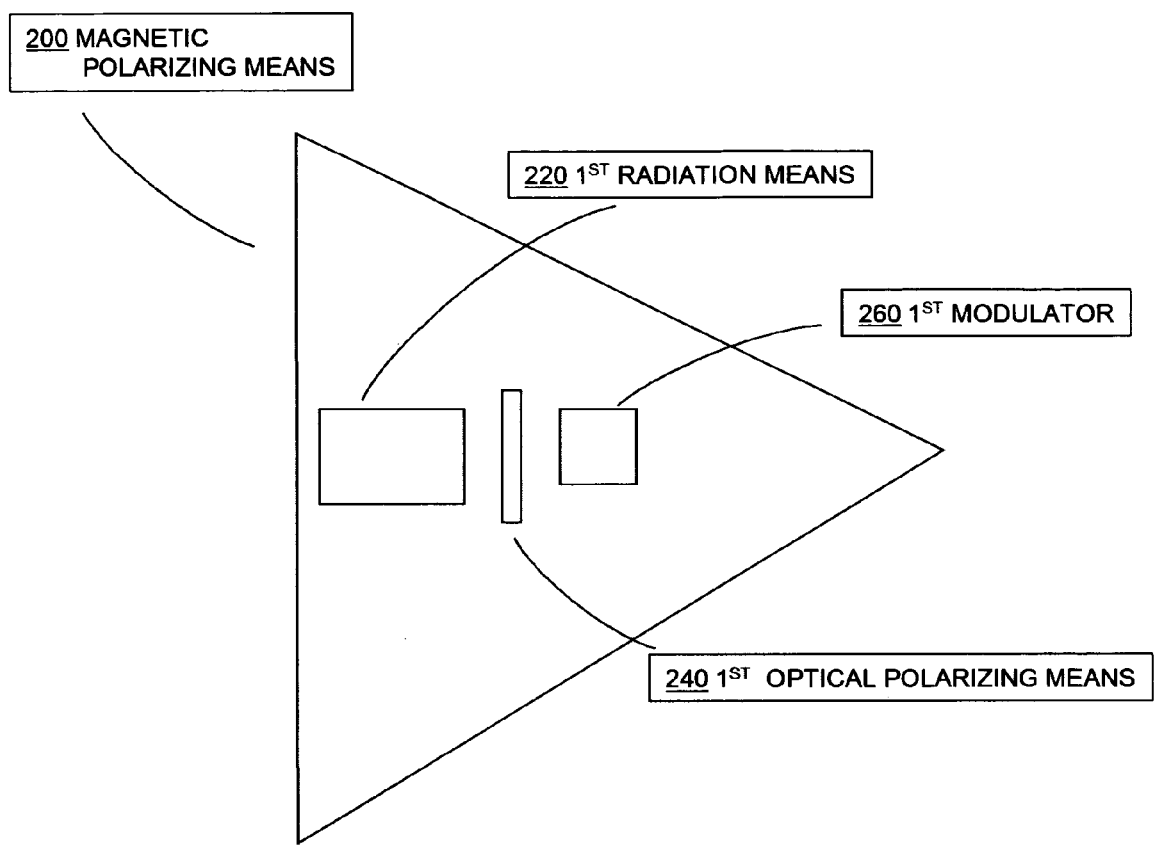
FIG. 2. Schematic diagram of several components employed in an embodiment of a means for increasing the magnetic polarization of an alkali metal vapor.

An important embodiment of the means for increasing the magnetic polarization of the alkali metal vapor 200 is exemplified in FIG. 2, which shows the means 200 in an expanded view. Encompassed within it is a first radiation generating means 220 that generates a first beam of radiation that is projected such that it illuminates the sensing cell and the alkali metal vapor contained within it. The energy of the first beam of radiation is sufficient effectively to increase the magnetic polarization of the alkali metal vapor. In an important embodiment, the first radiation generating means includes a first laser device. The attributes of the first laser device are such that it generates a beam of radiation whose radiation frequency and intensity are effective to increase the magnetic polarization of the alkali metal vapor. In order to attain a significant increase in the magnetic polarization of the alkali metal vapor, the first laser device is typically a high power laser whose radiation may be continuous or may be generated in pulses. The high power laser is frequently called an optical pumping laser, whose effect is to spin-polarize the alkali metal ions. Magnetization is commonly described in terms of components oriented along the orthogonal three Cartesian directions. As described herein, the direction of propagation of the first beam of radiation impinging upon the sensing cell is designated the z direction.

The performance of the present magnetometer is enhanced when the total rate of optical pumping and spin relaxation is greater than the bandwidth of signals to be detected. Additionally the magnetometer is beneficially operated when the total rate of optical pumping and spin relaxation is greater than the deviation of the magnetic field from zero times $\mu/h$. When the pressure of the buffer gas is sufficient the high power laser for the optical pumping may be a broadband diode laser.

In this embodiment, the means for increasing the magnetic polarization of the alkali metal vapor 200 further includes a first optical polarizing means 240 (FIG. 2) that polarizes the first beam of radiation. In various embodiments, first optical polarizing means provides linearly polarized radiation, or circularly polarized radiation, which may be left circularly polarized, right circularly polarized, or may alternate between left and right circular polarization. In addition, in certain other embodiments, the means for increasing the magnetic polarization of the alkali metal vapor 200 further optionally includes a first modulator 260 (FIG. 2) that modulates the first beam of radiation by a first modulation function. Such modulation, when employed, advantageously enhances the sensitivity of detection. Furthermore, different modulation functions may be applied to different parts of the polarizing beam. In this method different regions of the sensing cell experience different modulation conditions of the polarizing beam. These differences can be detected by the probe beam and be used to uniquely identify magnetic signals coming from different regions of the cell. In certain embodiments, a component that operates both to polarize the first beam of radiation and to modulate it may be incorporated into a single physical entity.

In additional significant embodiments of the magnetometer the pump beam used to increasing the magnetic polarization of the alkali metal vapor is tuned on resonance with the absorption of the vapor and is circularly polarized.

In general, any equivalent items of apparatus that operate to project energy onto the alkali metal atoms of the sensing cell in order to increase their magnetic polarization are encompassed within the scope of the means for increasing the magnetic polarization of the alkali metal vapor. Such modalities are known to workers of skill in fields related to the present invention, including by way of nonlimiting example, physicists, optical engineers, electrical engineers, and the like.

The atomic magnetometer of the present invention additionally includes means for probing the magnetic polarization of the alkali metal vapor 300 (FIG. 1). The probing means 300 interrogates the magnetic polarization of the vapor; the magnetic polarization in general includes a contribution resulting from the effect on the alkali metal atoms of a low intensity magnetic field intended to be measured by the atomic magnetometer. In this way the probing means induces the provision of an output that includes characteristics related to the low intensity magnetic field that the magnetometer is intended to measure. The output is provided after the probing means has interrogated the vapor.

Figure 3:
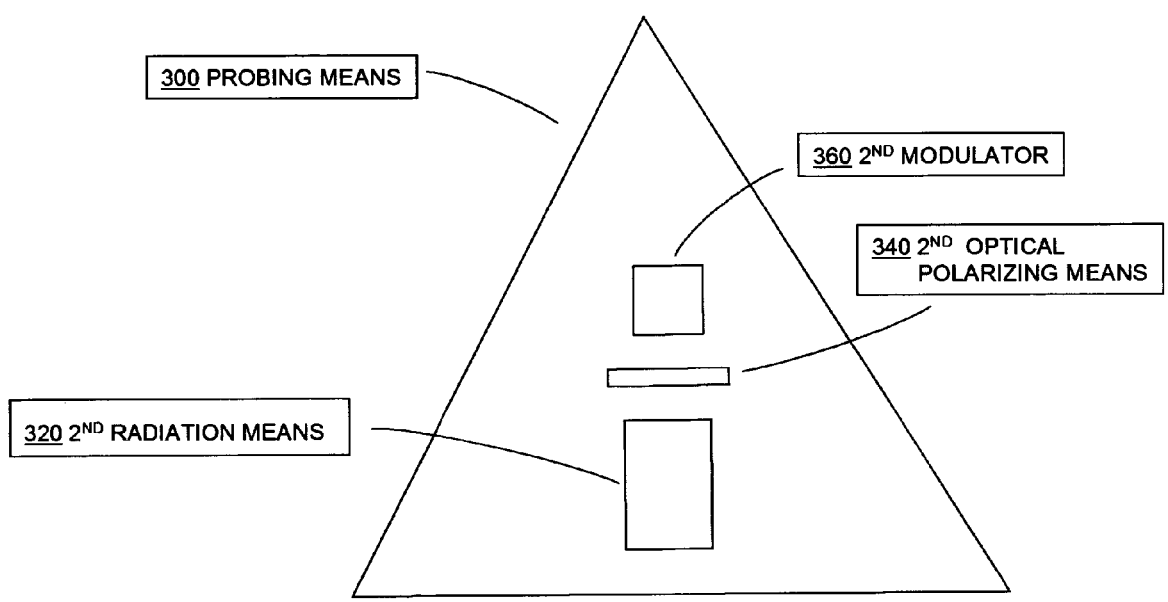
FIG. 3. Schematic diagram of several components employed in an embodiment of a means for probing the magnetic polarization of an alkali metal vapor.

An embodiment of the probing means 300 is further exemplified in FIG. 3. This embodiment includes a second radiation generating means 320 that generates a second beam of radiation traversing the alkali metal vapor. In advantageous embodiments the second radiation generating means includes a second laser. The frequency and intensity of the second beam of radiation are effective to interrogate the magnetic polarization of the alkali metal vapor without affecting the magnetic polarization significantly. In particular, its frequency differs from that of the first beam of radiation, being detuned from the resonance frequency of the vapor, sufficiently that no absorption occurs. In embodiments of the magnetometer employing Cartesian coordinates for description, a second beam of radiation impinges on and traverses the sensing cell in the x direction; additional second beams, polarized and modulated as described below, may impinge in other directions of the Cartesian coordinate domain.

In advantageous embodiments the means for probing the magnetic polarization of the alkali metal vapor 300 further includes a second optical polarizing means 340. In various embodiments the second optical polarizing means provides linearly polarized radiation, or circularly polarized radiation, which may be left circularly polarized, right circularly polarized, or may alternate between the two states. In addition, in certain other embodiments, the means for probing the magnetic polarization of the alkali metal vapor 300 further includes a second modulator 360 (FIG. 3) that modulates the second beam of radiation by a second modulation function. The second modulator advantageously serves to enhance the sensitivity of detection. When the pressure of the buffer gas in the sensing cell is sufficient the laser used for probing the magnetization of the alkali metal atoms may be a broadband diode laser.

In significant embodiments of the magnetometer the probe beam is tuned off resonance from the absorption of the alkali vapor, and is linearly polarized.

The output of the probing means is found after the probing means has traversed the sensing cell. In the embodiments described in the preceding paragraphs the output is constituted at least of the second beam of radiation after it exits the sensing cell. Its characteristic properties have been altered as a consequence of traversing the alkali metal vapor in a way that can be detected by appropriate means.

In general, an atomic magnetometer of the present invention includes a means for probing the magnetic polarization of the alkali metal vapor 300, or in significant embodiments it may include a plurality of means for probing the magnetic polarization of the alkali metal vapor, each of which is generally described as set forth above for a probing means 300. In the latter embodiments each means for probing the magnetic polarization of the alkali metal vapor 300 may project its probing energy on to the same sensing cell, or each separately may project its probing energy on to a separate sensing cell. Likewise, in embodiments having a plurality of means for probing the magnetic polarization of the alkali metal vapor 300, each such means directs its probing energy on to a separate measuring module 400 (see below).

In general, any equivalent items of apparatus that operate to project energy onto the alkali metal atoms of the sensing cell in order to interrogate their magnetic polarization are encompassed within the scope of the present invention. Such assemblies of apparatus are known to workers of skill in fields related to the present invention, including by way of nonlimiting example, physicists, optical engineers, electrical engineers, and the like.

The atomic magnetometer also includes magnetizing means 120 (FIG. 1) for imposing a probing magnetic field on a volume of space that includes the sensing cell. The probing magnetic field affects the magnetic polarization of the alkali metal vapor contained in the sensing cell and confers attributes thereon that contribute to the interrogation of the probing means. In many embodiments, the magnetizing means include induction coils through which an electrical current flows, thereby generating the probing magnetic field. In general, magnetizing means includes components oriented such that the probing magnetic field is provided in one, two, or all three of the orthogonal directions, x, y, and/or z. In this way all three components of the low intensity magnetic field vector being measured may be determined. Furthermore, in accomplishing this objective, the magnetizing means 120 may be driven by a third modulation function. As already indicated, as a result of the probing magnetic field present in the sensing cell, at least one property of the second beam of radiation is modulated as it traverses the alkali metal vapor experiencing the probing magnetic field. In addition the magnetizing means provides bias magnetic fields to the sensing cell that nullify residual background magnetic fields from the environment.

The sensitivity of the atomic magnetometer described herein is extremely high. For this reason all components of the magnetometer sensitive to magnetic fields must be effectively isolated from extraneous magnetic fields. Accordingly, a region of space that includes the sensing cell 100, the magnetizing means 120, and a region in which it may be intended to measure the magnetic field is enclosed in magnetic shielding, illustrated as 180 in FIG. 1. The magnetic shielding may be constructed of any of the widely known magnetic shielding substances, including by way of nonlimiting example magnetic shielding tape, Mollypermalloy, and μ metal; in addition magnetic shielding can include superconducting shields, which eliminate a Johnson noise component. The shielding is fabricated to allow the means for increasing the magnetic polarization of the alkali metal vapor and the means for probing the magnetic polarization of the alkali metal vapor to access the sensing cell and impinge upon it. Effective shielding and neutralization of background fields by the magnetizing means contribute to the enhanced sensitivity of the magnetometer of the present invention.

Any equivalent means of effectively shielding the region of space from extraneous magnetic fields is encompassed within the scope of the invention. Such equivalents are known in fields related to the present invention, including by way of nonlimiting example, physicists, optical engineers, electrical engineers, and the like.

Figure 4:
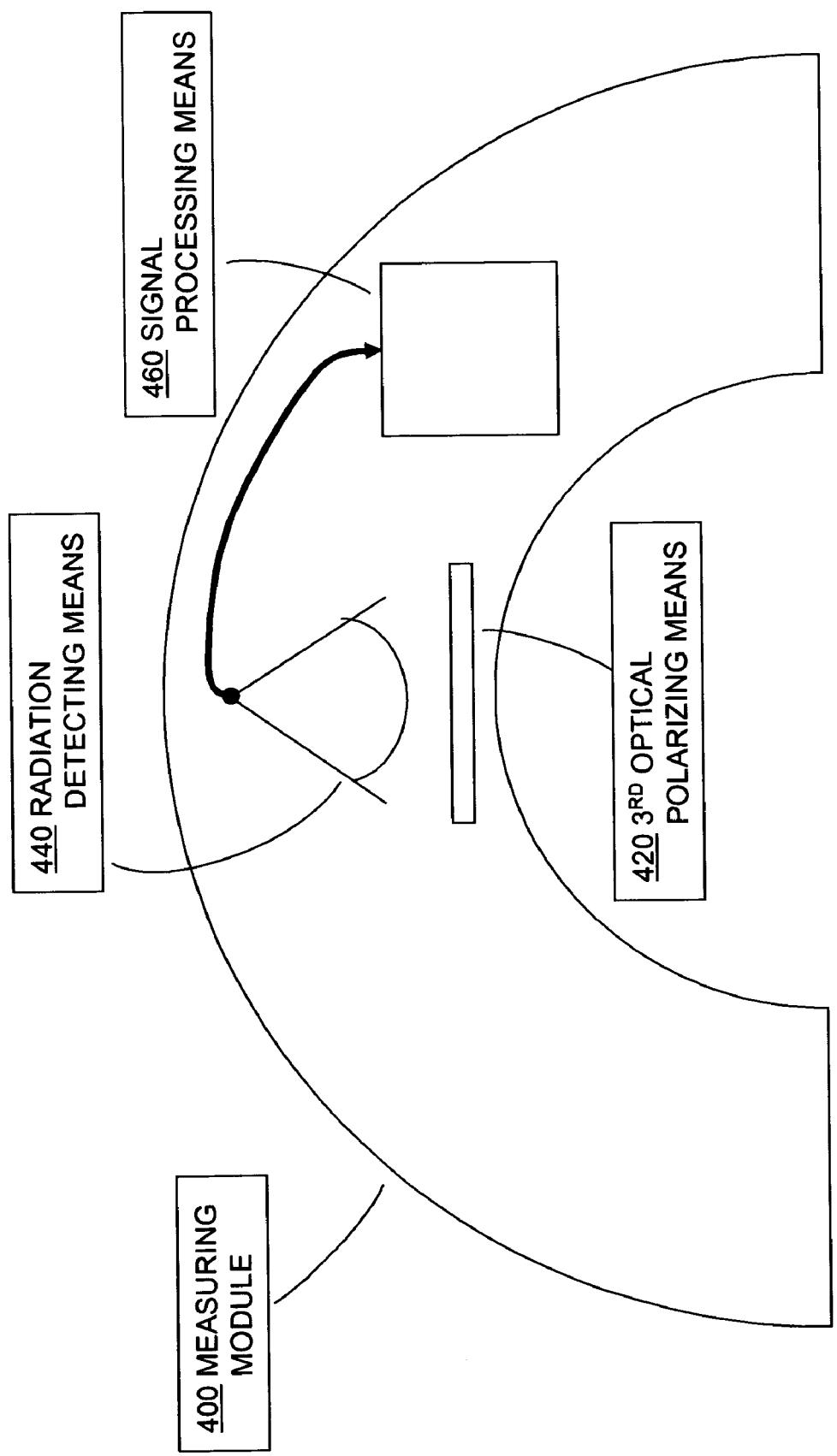
FIG. 4. Schematic diagram of several components employed in an embodiment of a measuring module.

The atomic magnetometer additionally includes a measuring module 400 (FIG. 4). Broadly the measuring module is a means for receiving the output after it is provided from the sensing cell, determining the characteristics of the low intensity magnetic field that are comprised in the output, and providing a representation characterizing the low intensity magnetic field detected by the sensing cell. In important embodiments the measuring means includes an output detecting means 440 (see FIG. 4) that provides a signal including characteristics related to the low intensity magnetic field, and signal processing means 460 for receiving the signal from the output detecting means 440 and providing the representation. Thus, in general, the output detecting means communicates with the signal processing means, such as is shown schematically by the heavy curved arrow in FIG. 4.

In those embodiments of the invention in which the probing means 300 includes a second radiation generating means 320 that generates a second beam of radiation traversing the alkali metal vapor, the output detecting means 440 includes a means for detecting radiation, such as the output of the second beam of radiation after the beam traverses the alkali metal vapor. Nonlimiting examples of radiation detecting means include a photometer, a photomultiplier, a photodiode or a photodiode array, a charge-coupled detector, a multichannel analyzer or array, and the like. In many embodiments in which a multiplexed detector such as a photodiode array or a multichannel analyzer or array is used, each detector in the array detects an output originating from a different region in the sensing cell. For optimal performance of a magnetometer employing multiplexed detectors in this way the pressure of the buffer gas is sufficient to limit diffusion of the alkali metal atoms between regions that provide outputs to different elements in the detector array.

Any equivalent means for detecting an output of the invention, including but not limited to equivalents for detecting radiation, are included within the scope of the present invention. Such equivalent detecting means are well known to workers of skill in fields related to the present invention, including by way of nonlimiting example, physicists, optical engineers, electrical engineers, and the like.

As noted above, many embodiments of the invention include means for probing the magnetic polarization of the alkali metal vapor 300 that also includes a second optical polarizing means 340. These may variously provide linearly polarized radiation, or circularly polarized radiation, which may be left circularly polarized, right circularly polarized, or may alternate between the two states. In such embodiments the measuring means 400 also includes a third optical polarizing means 420 (FIG. 4) interposed between the sensing cell and the radiation detecting means 440. In important examples, the third optical polarizing means may include a linear polarization analyzer or a circular polarization analyzer. Such analyzers are axially oriented to be at or near an extinction angle when there is no low intensity magnetic field that is to be measured impinging upon the sensing cell. In this way, the output detecting means is primed to detect a small amount of radiation different from zero, that includes characteristics of the low intensity magnetic field, to which it should be especially sensitive.

The radiation detecting means converts the output impinging upon it to a signal that includes components whose characteristics are related to the properties of the low intensity magnetic field. Such properties include, by way of nonlimiting example, spatial, temporal, amplitudinal, vectorial and similar properties it may be endowed with. The magnitude and time dependence are readily apparent in the characteristics of the signal in real time. In certain embodiments the vector components become apparent upon varying the imposition of a probing magnetic field by the magnetizing means 120 among the x, y, and z directions upon the sensing cell, and comparing the results obtained in the various cases.

The signal provided by the output detecting means, or at least a portion thereof, is input to the signal processing means 460. The signal processing means resolves characteristics related to the low intensity magnetic field from the signal and provides a representation attributes of the signal that are related to the low intensity magnetic field detected by the sensing cell. In important embodiments the signal processing means includes computing means that is programmed to resolve the characteristics related to the low intensity magnetic field from the input signal. The signal in general may include contributions sensed by the magnetic polarization of the alkali metal vapor from sources other than the low intensity magnetic field being determined, such as magnetic noise or optical noise. The computing means provides a representation of the characteristics of the low intensity magnetic field detected by the sensing cell. In important embodiments the computing means operates to minimize or eliminate components in the signal originating from noise.

As described above, in certain embodiments, a first modulator 260 that modulates the first beam of radiation by a first modulation function and/or a second modulator 360 that modulates the second beam of radiation by a second modulation function, may be employed. In such cases, the at least one signal comprises a component modulated by the first modulation function or by the second modulation function, or both. In those cases, the modulation function or functions provide reference information for the computing means, and the computing means detects only components in the signal that are modulated by the first modulation function or the second modulation function, or both.

When the output detecting means includes several radiation detecting means, such as occurs for example in a photodiode array, a multichannel analyzer, a charge coupled detector, and so forth, each element in the array provides a signal to the signal processing means. The signal processing means, for example, the computing means contained therein, provides a representation of the low intensity magnetic field sensed by each element in the array. Frequently, a first array element detects radiation traversing one region of the alkali metal vapor and a second array element detects radiation traversing a different region of the vapor. It is frequently advantageous to compare and process the signals originating in each region of the alkali metal vapor by operating as a gradiometer, and to compensate or nullify common components in them that are ascribed to optical or magnetic background, noise, or comparable extraneous sources. In this way a further enhancement of sensitivity of detection may be achieved.

The novel features and attributes of the atomic magnetometer described in the foregoing are effective to provide an apparatus with a high sensitivity for characterizing the low intensity magnetic field to be assessed. Broadly, the sensitivity is such that the magnetometer detects a magnetic field that is smaller than a predetermined value. In various embodiments, the predetermined value may be less than about 1 femtotesla $(Hz)^{-1/2}$, or less than about 0.5 femtotesla $(Hz)^{-1/2}$, or less than about 0.2 femtotesla $(Hz)^{-1/2}$, or less than about 0.1 femtotesla $(Hz)^{-1/2}$, or even less. In a theoretical assessment of the sensitivity of the magnetometer of the present invention, it is estimated that in optimal circumstances the limit of sensitivity may be as low as about 0.02 femtotesla $(Hz)^{-1/2}$ or 0.01 femtotesla $(Hz)^{-1/2}$. It is believed that such low limits of detection provide a level of sensitivity that is better than that of any magnetometer currently disclosed in the field.

Additional advantages of the instant magnetometer include the absence of a requirement for operation at cryogenic temperature, use of relatively inexpensive components, and relatively compact overall dimensions. The increased sensitivity furthermore permits the sensing cell to be kept to a size that is smaller than known in the field.

The atomic magnetometer described above may be used to detect and characterize low level magnetic fields from any source, provided the field produced by the source is apparent in the region of space occupied by the sensing cell. Sources of interest include geological specimens, forensic specimens, chemical specimens, industrial components, biological samples, and the like. An important requirement, as just noted, is that the field impinge on the sensing cell. Optimally this is achieved by placing a source or sample characterized by a low intensity magnetic field in the immediate vicinity of the sensing cell.

A particularly significant embodiment of the magnetometer of the invention is its modification to accommodate a living biological subject as the source of the low intensity magnetic field. The brain and other organs are sources of such fields, originating from the flow of electrical signals within them, and between their anatomical components. Measurement of brain magnetic fields by magnetoencephalography (MEG), for example using an apparatus of the present invention, should offer diagnostic potential that is equal to or better than comparable measurement such as electroencephalography. It is possible that other organs, including the heart, may also be characterized by measurable magnetic fields susceptible of observation by the present apparatus.

A high sensitivity atomic magnetometer of the present invention is suitable for use on a biological subject such as a mammal. It generates a representation of a primary magnetic field originating within a sample volume. The magnetometer is broadly similar to the magnetometer described in the foregoing in full detail. Generally it includes a) a sensing cell sensitive to low intensity magnetic fields comprising an alkali metal vapor and a buffer gas, the sensing cell being adjacent to a sample volume including a component generating a first magnetic field, wherein the sensing cell is exposed to a background magnetic field lower than a predetermined value;

b) means for increasing the magnetic polarization of the alkali metal vapor, wherein the magnetic polarization of the alkali metal vapor includes a contribution from the primary magnetic field;

c) magnetizing means for imposing a magnetic field on a volume of space including the sensing cell and altering the magnetic polarization of the alkali metal vapor;

d) means for probing the magnetic polarization of the alkali metal vapor, the probing means providing an output from the vapor including characteristics related to the first magnetic field; and e) measuring means for receiving the output, determining the characteristics of the first magnetic field, and providing a representation of the first magnetic field.

Figure 5:
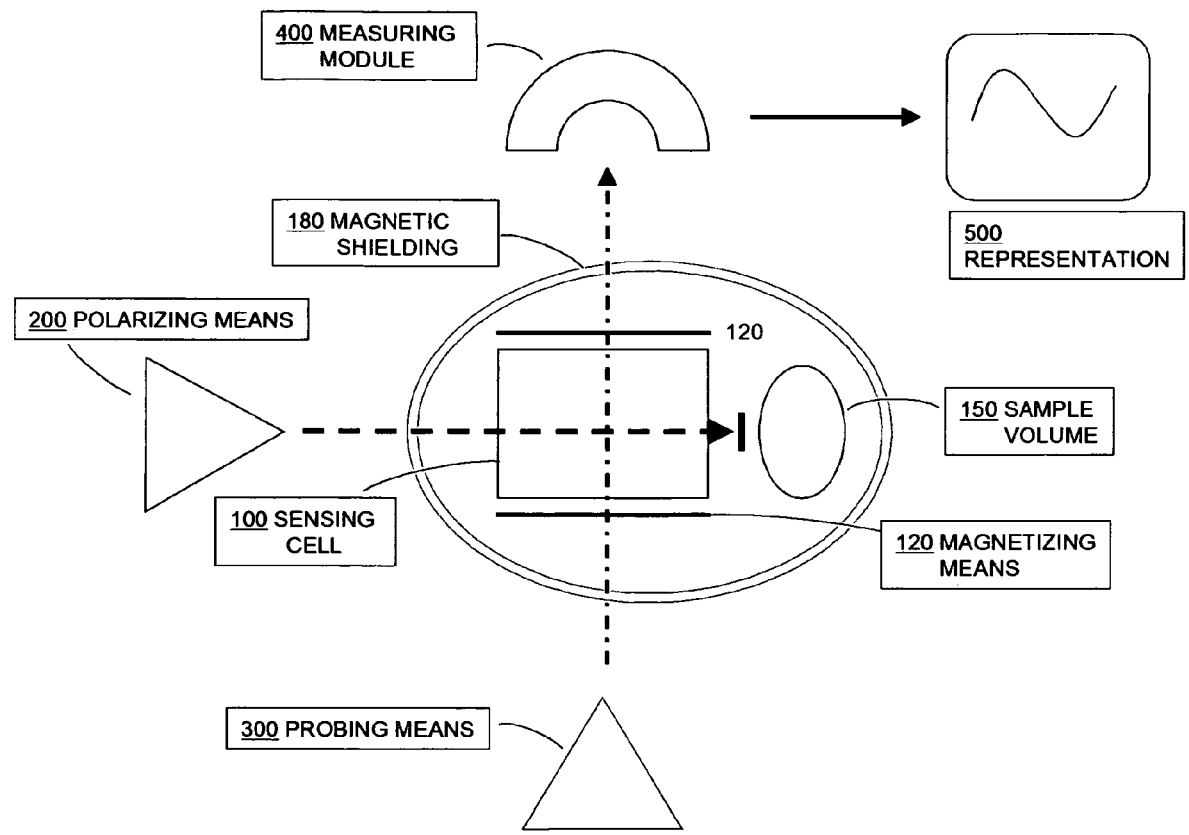
FIG. 5. Schematic diagram of several components employed in an embodiment of an atomic magnetometer of the present invention suitable for use on biological subjects.

Importantly, the sensing cell is adjacent to a sample volume including a component generating a primary magnetic field. The sample volume is represented in an embodiment of this aspect of the invention at 150 in FIG. 5. In the case of biological subjects, the sample volume includes at least a portion of a mammalian subject, such as the subject's brain or heart. In medical diagnostic applications the subject being studied is a human. In medical research applications the subject may be a nonhuman mammal or other animal. In constructing a magnetometer for use in applications such as these the apparatus advantageously places magnetic shielding 180 (FIG. 5) such that it encloses a region of space that includes at least the sample volume and the sensing cell, and includes as well the magnetizing means 120 (FIG. 5).

In important embodiments, including a high sensitivity atomic magnetometer useful on a biological subject, the signals from multiple photodetector elements are combined electronically to map magnetic fields and gradients. As an example, a two-dimensional photodetector array is used to obtain a 2-D representation of the magnetic field originating from the sample volume. Additionally, the energy beam of means for increasing the magnetic polarization of the alkali metal vapor may be scanned across the sensing cell to build a 3-D representation of the magnetic field. Similarly, common magnetic field modulation is utilized to measure independently and continuously all 3 Cartesian components of the magnetic field.

In operation, an atomic magnetometer of the invention is useful in a method for providing a representation of a low intensity magnetic field detected by a sensing cell that has high sensitivity to a magnetic field. Broadly the method includes the steps of:

a) providing an atomic magnetometer described in detail in the foregoing;

b) increasing the magnetic polarization of the alkali metal vapor contained in the sensing cell of the magnetometer, thereby increasing the sensitivity of the alkali metal vapor to a low intensity magnetic field;

c) reorienting the magnetic polarization of the alkali metal vapor using a magnetic field;

d) probing the magnetic polarization of the alkali metal vapor with a probing means of the magnetometer such as is described above, such that the probing means provides an output whose characteristics are related to the low intensity magnetic field; and e) receiving the output in a measuring means of the magnetometer, the measuring means operating on the output to provide a representation of the low intensity magnetic field detected by the sensing cell.

In an alternative embodiment of the invention, an atomic magnetometer described above may be employed in a method for providing a representation of a primary magnetic field originating within a sample volume. This method includes the steps of:

a) providing a high sensitivity atomic magnetometer described in detail in the foregoing;

b) identifying a sample volume that includes a source of the primary magnetic field adjacent to a sensing cell of the magnetometer;

c) increasing the magnetic polarization of the alkali metal vapor contained in the sensing cell, wherein the magnetic polarization of the alkali metal vapor includes a contribution from the primary magnetic field;

d) reorienting the magnetic polarization of the alkali metal vapor using a magnetic field;

e) probing the magnetic polarization of the alkali metal vapor with a probing means of the magnetometer, the probing means having the capability to provide an output, whose characteristics are related to the primary magnetic field; and f) receiving the output in a measuring means of the magnetometer, the measuring means operating on the output to provide a representation of the primary magnetic field detected by the sensing cell.

In this method the sample volume includes at least a portion of a mammalian subject. The embodiment of the atomic magnetometer employed in this method is constructed such that magnetic shielding is sufficient to enclose a region of space that includes the sample volume and a portion of a subject at least as large as the sample volume, the sensing cell, and a magnetizing means that provides a probing magnetic field.

In many important embodiments of this method for providing a representation of a primary magnetic field originating within a sample volume, a spatial image of the biological subject placed within the sample volume may be prepared. Such a representation arises, for example, when the magnetometer is used in MEG. In such embodiments, the representation includes a representation of a source of a magnetic field occurring within the sample volume displayed in one of three orthogonal Cartesian coordinates referenced to the sample volume, or in two such coordinates, or in all three coordinates, thus providing a linear, or a planar, or a spatial image of the sources of magnetic fields in the subject. The spatial resolution within the sample volume that is available in a representation may be 10 mm or better, or 5 mm or better, or 2 mm or better, or 1 mm or better, or 0.5 mm or better, or 0.2 mm or better, or even finer resolution.

As noted, the details of the atomic magnetometer employed in these methods, and in similar methods encompassed within the scope of the present invention, have been set forth in detail above, and are incorporated here by reference in entirety. In particular, by virtue of the characteristics of a magnetometer described herein, a method for providing a representation of a low intensity magnetic field, and a method for providing a representation of a primary magnetic field originating within a sample volume, can detect such a magnetic field with a sensitivity that is lower than a predetermined value. In various embodiments, the predetermined sensitivity may be less than about 1 femtotesla $(Hz)^{-1/2}$, or about 0.5 femtotesla $(Hz)^{-1/2}$, or about 0.2 femtotesla $(Hz)^{-1/2}$, or about 0.1 femtotesla $(Hz)^{-1/2}$, or even less. Without wishing to be bound by theory, a simulated assessment of the sensitivity of the magnetometer of the present invention provides an estimate that in optimal circumstances the limit of sensitivity may be as low as about 0.01 femtotesla $(Hz)^{-1/2}$.

Additional advantages of the methods of the present invention include their relative convenience and versatility. These advantages arise by virtue of the absence of a requirement for operation at cryogenic temperature, by use of relatively inexpensive components, and by relatively compact overall dimensions. The increased sensitivity furthermore permits the sensing cell to be kept to a relatively small size.

In view of these and related advantages of the magnetometers of the present invention, they are ideally suited for measuring the magnetic fields generated in biological subjects, such as the fields generated in the brain, the heart, and other organs with high currents developed by electrochemical gradients. The present magnetometers provide very high magnetic sensitivity, sufficient bandwidth, easy multi-channel operation, small "magnetic pixel" size, and the ability to detect different axial components of the magnetic fields. As an example, magnetic fields from the heart are also readily measured using the magnetometer.

EXAMPLES

Example 1

Potassium Vapor Atomic Magnetometer

An embodiment of a potassium vapor atomic magnetometer was constructed. The magnetometer consists of the following main components: magnetic shields with a shielding factor of $10^6$; field coils producing calibrated, uniform fields along $\hat{x}$, $\hat{y}$ and $\hat{z}$ directions and all five independent first-order field gradients; a glass sensing cell (3×4×3 cm) with flat windows, containing a drop of potassium (K) metal, 2.9 atm of $^4$He and 60 torr of $N_2$; a double-wall oven heated to 180° C. by flowing hot air to obtain a number density of potassium atoms in the vapour of n≈6×10$^{13}$ cm$^{-3}$; a circularly-polarised 1 W broadband diode laser ("pump" laser) tuned to the centre of the potassium D1 line at 770 nm for increasing the magnetic polarization of potassium metal vapor; a linearly polarised 100 mW single frequency laser ("probe" laser) detuned by 1 nm from the D1 resonance; a Faraday rotator modulating the plane of polarisation of the probe laser with an amplitude α≈0.02 rad at a frequency $f_{mod}$=2.9 kHz; beam-shaping optics, that produce a collimated probe beam with a cross section of 4 mm×19 mm; a polarisation analyser set orthogonal to the mean plane of polarization established by the Faraday modulator; a 7-element photodiode array (shown in the inset a), with element separation of 0.31 cm along the $\hat{y}$-direction; and a 16-bit data acquisition system using a digital 7-channel lock-in amplifier tuned to the frequency of the Faraday modulator to demodulate the signal proportional to the magnetic field $B_y$. Inset b provides a cross-section of the sensing cell showing the rotation of the magnetic polarisation P of the potassium atoms into the $\hat{x}$ direction by an applied magnetic field $B_y$. The plane of polarization of the probe beam is rotated in proportion to the $\hat{x}$ component of the spin polarization.

Figure 6:
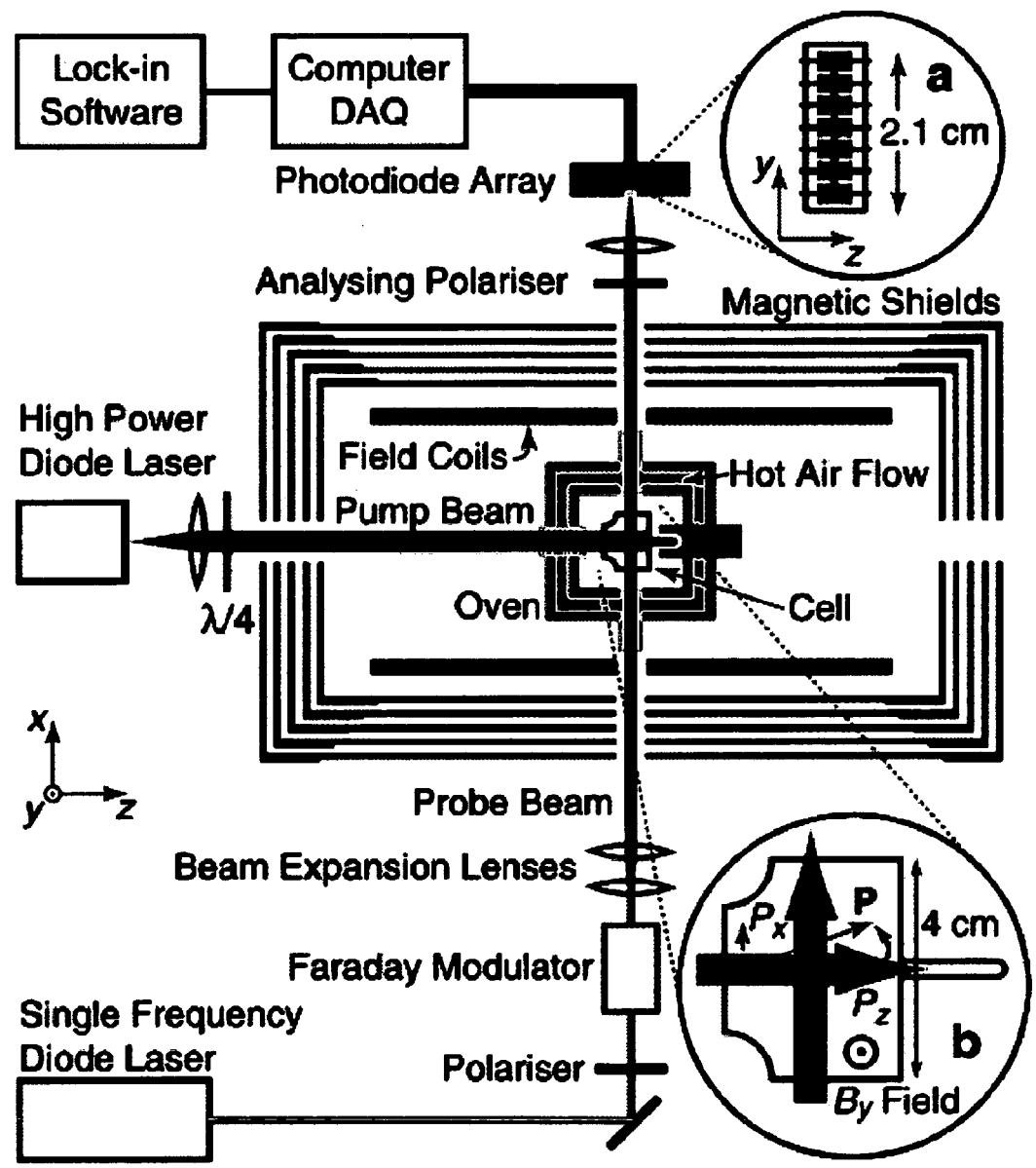
FIG. 6. Schematic diagram of an embodiment of the atomic magnetometer of the invention. Inset a, Expanded view of a photodiode array used to detect the probe beam. Inset b, Expanded view of the sensing cell showing generation of an x̂-component of polarization $P_x$ in response to a field $B_y$.

Using a multi-channel photo-detector (FIG. 6, inset a) the polarization of the probe beam and, therefore, of the $B_y$ field, is measured simultaneously at several adjacent points within the sensing cell. The magnetometer is operated with all three components of the magnetic field close to zero. It is believed that under these conditions the signal is not sensitive to small changes in $B_x$ and $B_z$ fields, and the device operates as a vector magnetometer. By taking a linear combination of the signals measurements of the first and higher order gradients of the magnetic field can be made (see Examples 2 and 3).

Example 2

Estimation of the Intrinsic Magnetic Noise Level

A simulation of the noise level that may be expected in an atomic magnetometer such as described in Example 1 was carried out. Without wishing to be bound by theory, it is believed that the fundamental, shot-noise-limited sensitivity of an atomic magnetometer is given by $$\delta B = \frac{1}{\gamma\sqrt{nT_2 V t}}, \quad (1)$$

where n is the number density of atoms, γ is their gyromagnetic ratio, $T_2$ is the transverse spin relaxation time, V is the measurement volume, and t is the measurement time (Budker D. et al., *Rev. Mod Phys.* 74, 1153–1201 (2002).) The value of γ in Eq. (1) depends on the details of the magnetometer operation. For a commonly used ΔAm=1 transition γ=gμ$_B$/((2I+1)(h/2π)), where I is the nuclear spin of the alkali metal and m is its nuclear spin state. In a magnetometer such as described in Example 1 operating at zero field the effective γ for sensitivity estimates is γ=gμ$_B$/(h/2π) (Eq. (7) of Allred, J. C. et al., *Phys. Rev. Lett.* 89, 130801 (2002)).

The magnetometer of the present invention is free of spin-exchange relaxation, for the broadening due to spin-exchange collisions is completely eliminated by operating at a high alkali metal density in a very low magnetic field. The remaining broadening is determined by spin-relaxation collisions, which have much smaller cross-sections compared to spin exchange, yielding theoretical limits on magnetic field sensitivity below 0.01 fT/Hz$^{-1/2}$ in 1 cm$^3$. However, to realize such sensitivity in practical applications usually requires operating the device as a magnetic gradiometer to cancel common-mode magnetic field noise. By adding $^4$He buffer gas to the magnetometer cell the diffusion of the K atoms is slowed. As a result the magnetometer can be operated as a multi-channel instrument with high sensitivity and adjacent channel spacing of only 3 mm. This allows cancellation of ambient magnetic field noise and permits magnetic source localization with high spatial resolution.

Figure 7:
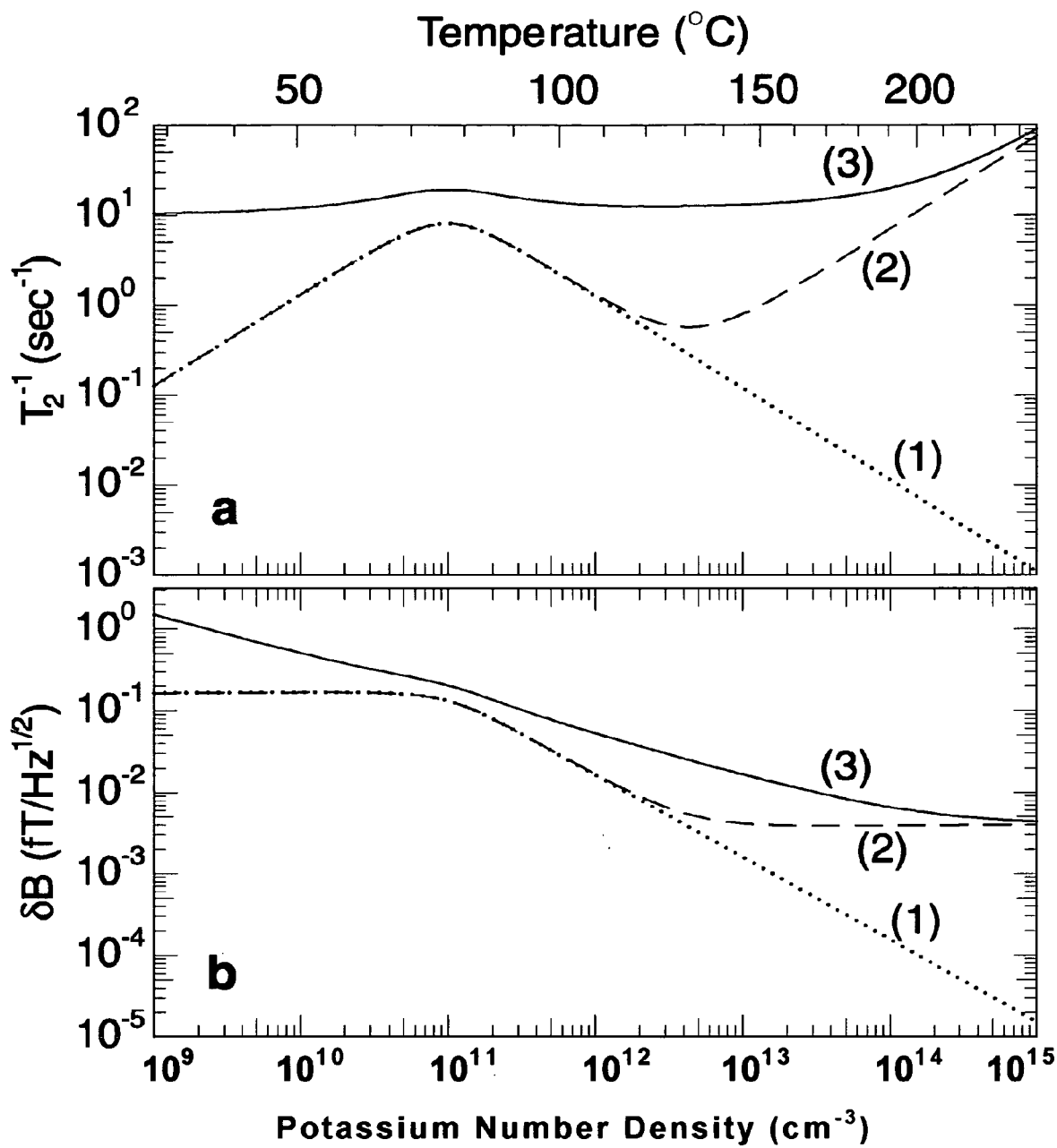
FIG. 7. Simulation of relaxation rate and theoretical magnetic field sensitivity of an atomic magnetometer of the invention. Panel a, Estimate of the transverse relaxation rate $1/T_2$. Panel b, Estimated magnetic field sensitivity shot-noise limit for a measurement volume V=0.3 cm$^3$.

The theoretical sensitivity of the magnetometer as a function of K density is shown in FIG. 7, including the effects of spin-exchange and spin-relaxation due to K—K and K—He collisions. Panel a illustrates an estimate of the transverse relaxation rate 1/$T_2$ due to alkali metal spin-exchange collisions (Happer, W. et al., *Phys. Rev. A* 16, 1877–1991 (1977)) in a small magnetic field B=10 μG (curve 1), spin-exchange and K—K spin-relaxation collisions (curve 2), and an estimate that is the same as curve 2 with the addition of K—He collisions for 2.9 atm of $^4$He gas (curve 3). Panel b shows estimates for the magnetic field sensitivity shot-noise limit for the cases of curves (1)–(3) obtained from Eq. (1) with a measurement volume V=0.3 cm$^3$. A volume as small as this would correspond to one observation element in a probe beam detected with one element in an array detector. It is seen from panel b that, when the operating density is about 10$^{13}$ or greater, as would be case in most implementations, a sensitivity of about 10$^{-2}$ fT/(Hz)$^{-1/2}$ or less is anticipated.

These simulations far surpass the performance of most atomic magnetometers known in the field that use a polarized alkali-metal vapor (K, Rb, Cs). Their transverse spin relaxation times are limited by spin exchange collisions between alkali atoms. For example, in one implementation of such a magnetometer (Budker, D. et al., *Phys. Rev. Lett.* 81, 5788–5791 (1998).; Budker, D. et al., *Phys. Rev. A* 62, 043403 (2000).) the shot-noise sensitivity was estimated to be 0.3 fT/Hz$^{1/2}$ for a 500 cm$^3$ cell. In another known magnetometer (Aleksandrov, E. B. et al., *Optics and Spectr.* 78, 292–298 (1995)) the actual sensitivity was estimated to be 1.8 fT/Hz$^{1/2}$ with a bandwidth of about 1 Hz and a measurement volume of 1800 cm$^3$.

This simulation also exceeds the performance of gradiometer operation of previous atomic gradiometers. For example, Aleksandrov et al. used two identical magnetometers with a baseline on the order of 1 meter (Alexandrov, E. B., *Laser Phys.* 6, 244–251 (1996)), which is highly unwieldy and impractical, or in another implementation had poor magnetic field sensitivity of about 4 pT/Hz$^{1/2}$ (Affolderbach, C. et al., *Appl Phys B* 75, 605–612 (2002)). In another magnetic gradiometer implementation (Bison et al. Appl. Phys. B. 76, 325 (2003) and Bison et al. Opt. Expr. 11, 908 (2003)), magnetic gradient sensitivity of about 1 pT/Hz$^{1/2}$ was obtained while the intrinsic sensitivity of the gradiometer was estimated to be 100 fT/Hz$^{1/2}$.

Example 3

Experimental Determination of the Magnetic Noise Level

Figure 8:
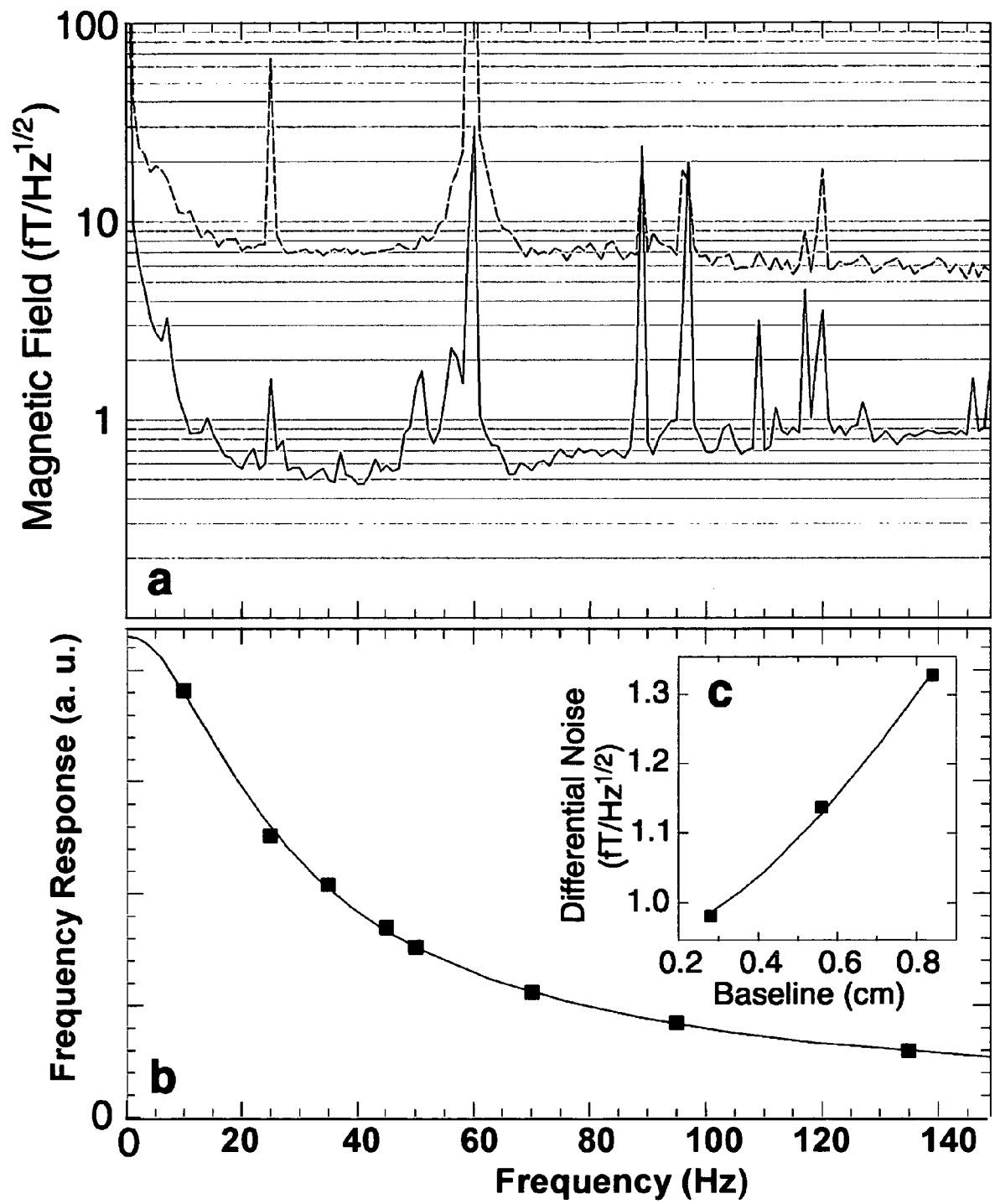
FIG. 8. Magnetic field sensitivity and bandwidth of the magnetometer of Example 3. Panel a, magnetic field noise in a single channel (dashed line) and intrinsic magnetic field sensitivity of a single channel extracted from the difference between adjacent channels (solid line). Panel b, absolute field sensitivity. Panel c (inset), magnetic field noise in the channel difference as a function of the distance between channels.

Using the potassium vapor magnetometer described in Example 1, the frequency dependence of the noise level in a single magnetometer channel was evaluated. The result is shown in FIG. 8, panel a, by a dashed line. The single-channel magnetometer noise is dominated by thermal Johnson currents in the μ-metal shields (Nenonen, J. et al., *Rev. Sci. Instr.* 1996; 67: 2397–2405). A first-order gradiometer was formed by taking the difference between two adjacent magnetometer channels. This procedure cancels the common magnetic field noise. Assuming the remaining noise is uncorrelated, the resulting noise level was divided by $\sqrt{2}$ to obtain the intrinsic magnetic field sensitivity of each channel. The response of the magnetometer was recorded for about 100 sec, performing a fast Fourier transform (FFT; without windowing) and calculating r.m.s. amplitudes in 1 Hz bins. The resulting gradiometer sensitivity is shown by the solid line in FIG. 8, panel a. To obtain absolute field sensitivity the magnetometer FFT was divided by a normalized frequency-response function shown in (b) (see below) with a fit to $A/(f^2+B^2)^{1/2}$, where the bandwidth B=20 Hz. Apart from a number of sharp peaks from technical sources of noise (including a peak due to the calibrating B$_y$ field at 25 Hz, and the fundamental and harmonic of the line frequency at 60 Hz), the magnetic noise level is less than 1 fT/Hz$^{1/2}$ in the range of 10 to 150 Hz and averages to 0.54 fT/Hz$^{1/2}$ in the range of 28–45 Hz. The active measurement volume probed by each channel was only 0.3 cm$^3$. The inventors believe this represents the highest magnetic field sensitivity obtained in either superconducting or atomic magnetometers known in the field, and is therefore unexpected by a skilled artisan in this and related fields.

The magnetometer frequency response, shown in FIG. 8, panel b, was measured by applying a known oscillating B$_y$ field at several frequencies. The frequency response depends on the optical-pumping and spin-relaxation rates (Allred, J. C *Phys. Rev. Lett.* 89, 130801 (2002)) and is well described by a single-pole, low-pass filter with a cut-off frequency of about 20 Hz.

FIG. 8, panel c, shows the magnetic noise in the difference between two channels as a function of the distance between them, that is, the baseline of the gradiometer. The probe beam slightly expands in the $\hat{y}$ direction, so the channel spacing is 0.28 cm, 10% smaller then the photodiode element separation. The noise is expected to increase with the baseline d of the gradiometer due to the magnetic field gradient noise. The fit of the form $N=\sqrt{N_1^2+N_2^2+d^2G^2}$, where $N_1$ and $N_2$ are the intrinsic noise levels in each channel, gives a magnetic field gradient noise G=1 fT/cm Hz$^{1/2}$, which is somewhat larger than the estimate of 0.5 fT/cm Hz$^{1/2}$ for the gradient noise produced by the magnetic shields (Nenonen, J. et al., *Rev. Sci. Instr.* 1996; 67: 2397–2405). This probably indicates that some noise comes from local sources—perhaps the metal in the temperature sensor near the cell. A second-order gradiometer can also be formed using 3 adjacent channels. The intrinsic sensitivity of each channel measured in this way is slightly better but the improvement is not significant.

Example 4

Operation of a Magnetometer in a Multi-channel Imaging Mode

Figure 9:
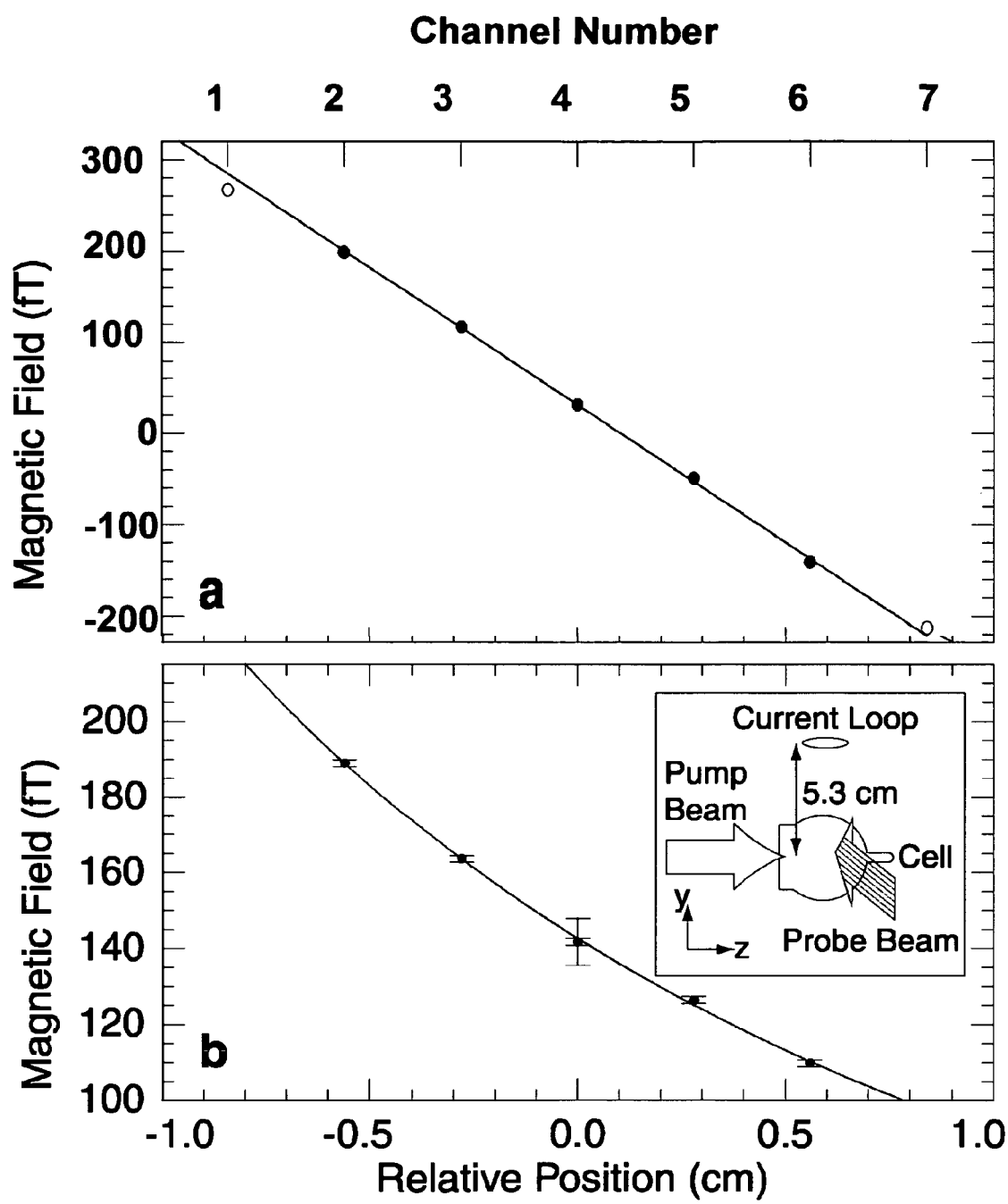
FIG. 9. Localization of a small coil using magnetic gradient imaging. Panel a, measured response for an applied uniform gradient $dB_y/dy=315$ fT/cm oscillating at 25 Hz. Panel b, measured response from a magnetic dipole $\mu=1.25$ $\mu A\,cm^2$ located 5.3 cm away and oscillating at 25 Hz with the magnetic dipole field fit. The large error bar on the middle data point represents the single channel noise level after 1 sec of integration. The small error bars represent the noise in the relative signal between adjacent channels. The inset in panel b diagrams the disposition of the field-generating current loop with respect to the sensing cell.

The magnetometer described in Example 1 has been operated in a multi-channel imaging mode. First a uniform oscillating magnetic field gradient dB$_y$/dy was applied to check the linearity of the device, as shown in FIG. 9, panel a. With the exception of the outer channels, which are not fully illuminated by the pump laser, the response was found to be quite linear and the measured gradient agrees to within 4% with the strength of the applied gradient.

To simulate a biological source a small coil was placed about 5.3 cm from the center of the magnetometer. An oscillating current was applied to the coil with a frequency of 25 Hz to generate a magnetic dipole μ=1.25 μA cm$^2$ and the data were analyzed in 1 sec intervals (see FIG. 9, panel b inset). The results are shown in FIG. 9, panel b. The data were fitted to the magnetic dipolar field profile. The large error bar on the middle data point represents the single channel noise level after 1 sec of integration. The small error bars represent the noise in the relative signal between adjacent channels. The results show that after 1 sec of averaging the uncertainty in the distance to the dipole is 2 mm and the uncertainty in its absolute size is 13%.

The spatial resolution of the magnetic field measurements inside the magnetometer cell is limited by the diffusion of the K atoms. Based on a detailed model of the diffusion in the presence of the buffer gas the resolution was estimated to be about 2 mm for the present conditions, slightly smaller than the spacing between the channels. The accuracy of localization of magnetic field sources outside of the magnetometer depends on a number of factors including the signal-to-noise ratio, distance from the magnetometer, and the uniformity of the magnetometer response. These factors can be analyzed and optimized in routine fashion by a skilled artisan. Typically the spatial distribution of magnetic field sources can be localized to loci that are a fraction of the detector size. A localization uncertainty on the order of 0.2 mm is predicted for the present magnetometer for sufficiently high signal-to-noise ratio. It is believed that the high level of spatial resolution provided by the instant magnetometer is unexpectedly better than has been attained in atomic magnetometers in use at the time the present invention was made.

Example 5

Mapping the Magnetic Fields Along 3 Orthogonal Directions

The magnetometer described in Example 1 has also been used to simultaneously and independently detect magnetic fields along 3 orthogonal directions. By applying small modulations to the magnetic fields using external coils and detecting the response of the system by the imposed modulation function it was found possible to separately measure all three components of the magnetic fields. This technique allows building a detailed vector map of the magnetic field over the measurement volume.

Example 6

Magnetometer Suitable for use in Magnetoencephalography of Human Subjects

Figure 10:
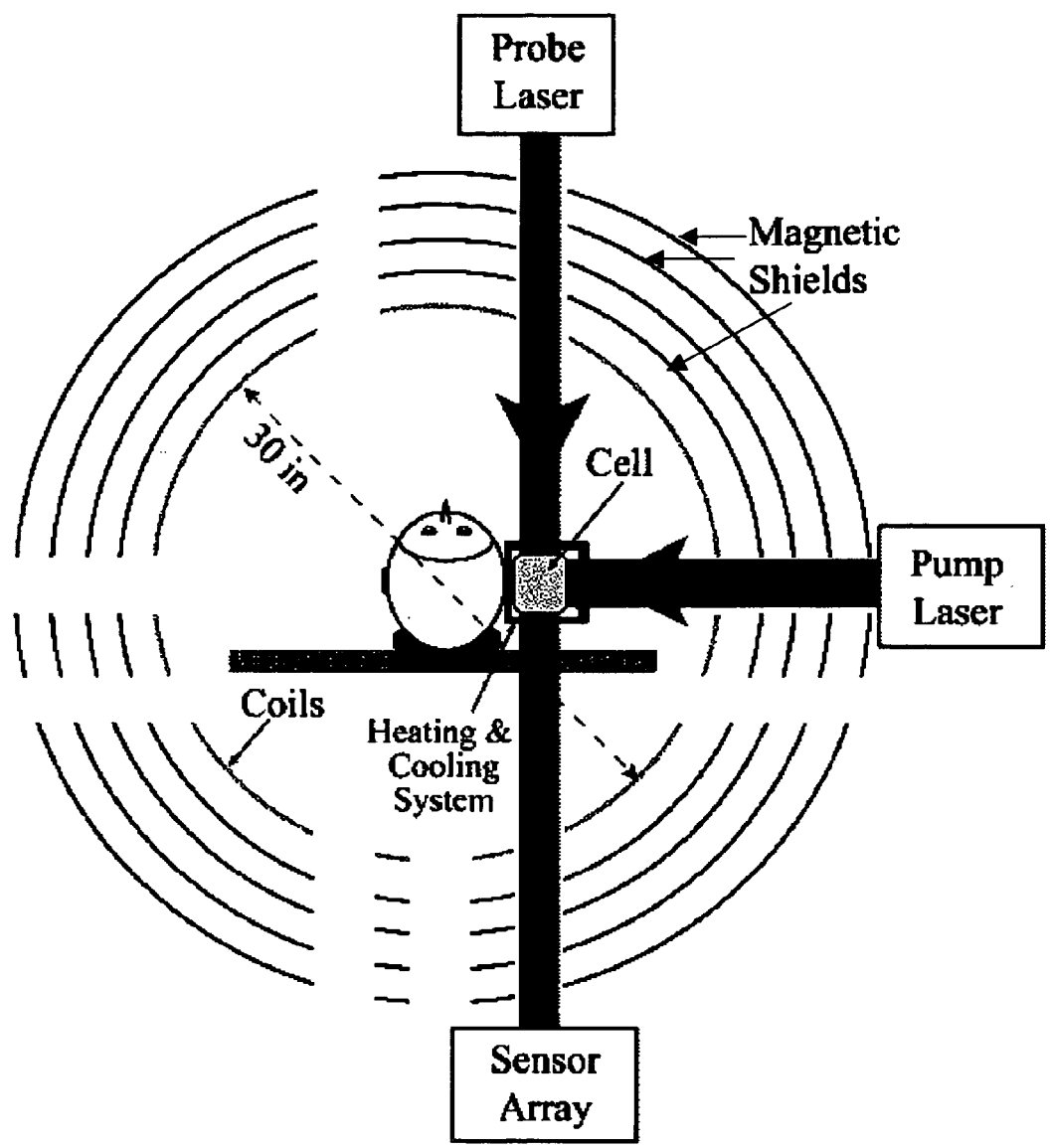
FIG. 10: Schematic diagram of an embodiment of an atomic magnetometer of the invention suitable for use in MEG on a human subject.

An atomic magnetometer for MEG studies intended for use with human subjects uses larger magnetic shields, better thermal management, and increased cell size. A schematic diagram of a magnetometer useful for human MEG is shown in FIG. 10.

Magnetometer Components

Measurement Cell

A glass sensing cell containing K atoms and He buffer gas defines the magnetic field measurement region. The cell is made from aluminosilicate glass that is chemically resistant to alkali metals and impermeable to He gas. Flat glass plates with high optical transmission are fused to form a cubical cell approximately 10 cm on a side. After the cell is evacuated and baked out at 400° C. a small amount of K metal is distilled into the cell. Then it is filled with 1–2 atm of $^4$He gas to reduce diffusion of K atoms, and with 60 torr of $N_2$ needed for quenching during the optical pumping process.

Pump Laser (Polarizing Laser)

The pump laser develops several watts of power to fully polarize K atoms in a large cell by optical pumping (W. Happer, *Rev. Mod Phys.* 1972, 44:169–249). Relatively inexpensive broadband diode lasers can be used for optical pumping. The laser is tuned to the center of the potassium D1 absorption line at 770 nm and circularly polarized using a quarter-wave plate.

Probe Laser

The magnetic field originating in the sample volume is measured by detecting the direction of the K electron spin polarization using a probe laser orthogonal to the pump direction. The probe laser is linearly polarized and detuned to the side of the absorption resonance. The probing light is not significantly absorbed by the atoms, thus ensuring uniform sampling of the entire cell. K atoms cause an optical rotation of the plane of polarization of the probe light proportional to the magnetic field. To eliminate optical pumping by the wings of the laser emission profile the laser beam may be first passed through an optically-thick K cell that will absorb all resonant radiation.

The magnetometer bandwidth is set by the optical pumping and relaxation rate R, which includes contributions from absorption of pumping and probing light and from spin relaxation processes in the cell. The optimal sensitivity is achieved when the laser absorption rates are comparable to the intrinsic spin-relaxation rates. However, a higher bandwidth can be obtained by increasing the optical pumping rate beyond this optimal point without a great loss in sensitivity. In the recent measurements the bandwidth was set to about 20 Hz but a good signal/noise ratio was obtained up to 150 Hz. For MEG data collection the bandwidth will be increased to reduce the distortions of the magnetic signals, although the distortion could also be corrected using digital filters. The bandwidth can be easily increased to 100 Hz by increasing the optical pumping rate. It is estimated that about 10 W of broadband laser power, which can be obtained from a diode laser, is needed for optical pumping of K atoms. The power of the probe laser is similar. The density of K atoms will also be increased slightly since a higher spin-relaxation rate can be tolerated. The K cell is maintained at 200° C. to achieve density of about $1.5 \times 10^{14}$ cm$^3$. Thermal insulation requirements for keeping a human subject adjacent to the sensing cell are easily satisfied by removing the excess heat with active water cooling.

Measurement of Rotation a. Faraday modulation. The optical rotation of the polarization plane is measured by a Faraday modulation technique. Prior to passing through the sensing cell the plane of the polarization of the probe beam is modulated using a Faraday modulator with an amplitude $\alpha_m \sim 2°$ at a frequency $\omega_m = 2\pi \times 5$ kHz. After the beam passes through the cell, it goes through a polarization analyzer set at 90° (extinction) with respect to the initial plane of polarization. The transmitted intensity is given by:

$$I = I_0 \sin^2[\alpha_m \sin(\omega_m t) + \phi] \cong I_0[\alpha m_m^2 \sin^2(\omega_m t) + 2\alpha_m \phi \sin(\omega_m t) + \phi^2]$$

where $\phi$ is the polarization rotation angle induced by the atoms. It follows that the amplitude of the oscillations in transmitted intensity after the analyzer at the frequency $\omega_m$ is proportional to $\phi$ and, therefore, to the magnetic field.

This measurement technique has the advantage of giving a signal at high frequency so it is not affected by 1/f technical noise. On the other hand it requires a higher rate of data acquisition and a digital demodulation of the signal.

b. Alternative measurement of polarization. Other techniques for detection of the optical rotation may be developed, such as use of two overlapping laser beams detuned to either side of the absorption resonance. The polarizations of the beams are rotated in opposite directions by the atoms. Subtracting the transmitted intensities allows canceling 1/f noise and measuring the optical rotation using a simpler method.

Photodiode Array

The transmitted intensity of the probe beam after the polarization analyzer is measured using a photodiode array. A 16×16 photodiode array manufactured by the Hamamatsu Corporation is used. Simple optics is used to image the probe beam on to the array. Each element of the array has a dedicated amplifier with appropriate frequency filters and a dedicated data acquisition channel.

The three main optics subsystems: pump laser, probe laser, and sensor array are made into compact self-contained modules that can be mounted in several positions around the shielding. Depending on the orientation of the lasers and the sensing cell different regions of the brain can be studied and different components of the magnetic field can be easily measured. Additional cells, pump, probe, and detection modules may be included to achieve full-head coverage.

Magnetic Shielding

Since the magnetometer does not require a large liquid helium dewar it can operate in a whole-body magnetic shield that would have a higher shielding factor and would be much cheaper than a shielded room typically used for SQUID magnetometers. Magnetic shields are constructed that are sufficiently large to accommodate a human in supine position using an inner layer of METGLAS tape and 3 cylinders of regular µ-metal.

General principles of passive magnetic shielding are well-established (Kelha V. O. et al., *IEEE Trans. Magn.* 1982; 18: 260–270) and magnetically shielded rooms are commonly used for MEG imaging. Their shielding factors are typically on the order of 1000 at frequencies below 1 Hz and increase rapidly with frequency. Such shielding is usually sufficient to attenuate most sources of external magnetic noise. Ultra-sensitive magnetometers are often limited by a more fundamental source of magnetic noise generated by thermal Johnson currents flowing in conductive materials, including magnetic shields (Nenonen, J. et al., in Biomagnetism '87, Ed. K. Atsumi et al., (Denki University Press, Tokyo, 1988), p. 426). This is a particular problem for SQUID sensors which must be located in dewars that contain thin conductive foils for radiation shielding. Thermal radiation shielding is not necessary for the present atomic magnetometer since it does not rely on cryogens.

The dominant source of magnetic noise is due to thermal currents flowing in the magnetic shields. The Johnson noise is reduced by increasing the electrical resistivity of the shielding material, decreasing its thickness, and breaking the material into small patches electrically insulated from each other. For example, thin METGLAS magnetic tapes appear ideal from this point of view. Preliminary theoretical analysis suggests that magnetic noise levels down to 0.1 fT/Hz$^{1/2}$ may be achieved in certain shield configurations. Magnetic shielding can be constructed as well taking advantage of superconducting shields, which do not have a Johnson noise component.

Heating and Cooling System

Figure 11:
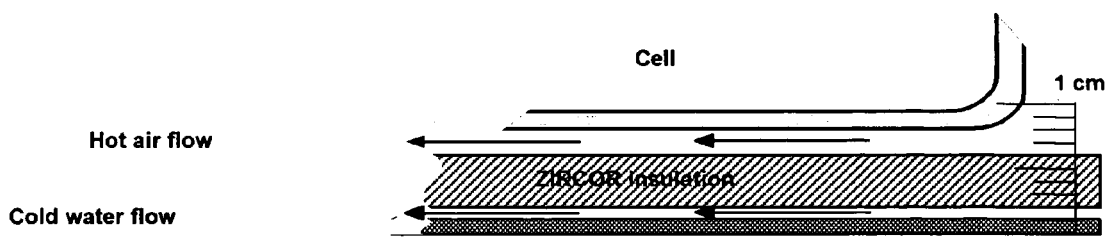
FIG. 11: Schematic diagram showing a cutout of the sensing cell corner and the thin wall of the oven facing a portion of the body of a subject.

To achieve optimal density of K vapor the sensing cell is heated to 180–200° C. An appropriate heating and cooling system to maintain the outside surface of the sensor at room temperature is achieved by water cooling. No conductive materials can be used because they generate Johnson magnetic noise. To reduce the thickness of one of the walls of the oven to 1 cm an advanced insulation ceramic, such as ZIRPOR, with thermal conductivity of 0.02 W/m · ° C., is to be used. Heating on one side is achieved with flowing hot air while cooling on the other side with a sheet of flowing water, as shown in FIG. 11. A system of temperature sensors and interlocks is to ensure that the outside wall of the sensor is always maintained at room temperature.

Data Acquisition System

The magnetic field is probed using a 16×16 photodiode array from Hamamatsu. A commercial simultaneous-sampling data acquisition system with 256 channels is used for recording of the data After digitization the signals are passed through a digital lock-in amplifier, referenced to the modulation frequency imposed by the modulator, to extract magnetic field data. The real-time analysis is done by a dual-processor PC workstation. A separate digital-to-analog board is used to control magnetic fields and stimulation devices.

Software

Software is to be developed for calibration of all channels, analysis of linear combinations of different channels operating as synthetic gradiometers, and nonlinear fitting to the spatial field distributions for localization of magnetic field sources. In addition the data are convertible for use with existing neuroimaging software packages.

Operation of the Magnetometer

Without wishing to be bound by theory, it is believed that the behavior of the spins in the sensing cell can be understood based on simple Bloch equations $$\frac{d\vec{P}}{dt} = -\gamma \vec{B} \times \vec{P} - R(\vec{P} - \vec{P}_0),$$

where $\gamma$ is the gyromagnetic ratio of K atoms, R is the optical pumping and relaxation rate, and $P_0$ is the equilibrium K polarization parallel to the pump laser direction. Taking the pump laser direction as $\hat{z}$ and probe laser direction as $\hat{x}$ it is found that optical rotation angle $\phi$ is proportional to $P_x$, which in a steady state is given by $$P_x = \frac{B_x B_z + B_y R/\gamma}{B_x^2 + B_y^2 + B_z^2 + (R/\gamma)^2} P_0.$$

The magnetometer is operated with all 3 magnetic field components much less than $R/\gamma \sim 10$ nT. Small background fields are zeroed using compensation coils. In this regime the magnetometer is primarily sensitive to the $B_y$ field component.

Figure 12:
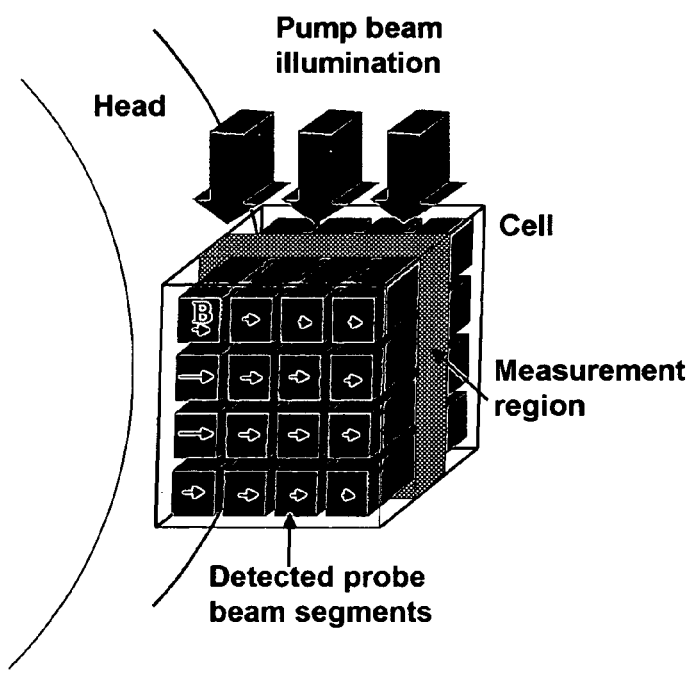
FIG. 12. Schematic diagram showing an arrangement of pump and probe laser beams and the measurement region in a sensing cell at their intersection. In the absence of field modulation the magnetometer is sensitive to the magnetic field normal to the head a subject in the sample volume.

As a result of these considerations, it is believed that the magnetometer is sensitive in first order to the magnetic field perpendicular to both pump and probe beams. FIG. 12 shows a possible arrangement of the laser beams that would allow measurements of the magnetic field normal to the head. Simply rotating the pumping laser by 90° so it points toward the head allows measurements of the tangential component of the magnetic field. The magnetic field is easily measured as a function of two co-ordinates using a two-dimensional detector array. In the third dimension the measurement region is defined by the pumping laser. Scanning of the pumping laser across the cell allows building a three-dimensional map of the magnetic field for repetitive brain signals. In addition, 3-dimensional snapshots of the magnetic field are made using pump laser modulation techniques.

Example 7

Optimizing Bandwidth and Sensitivity of Detection of the Magnetometer for use in MEG.

The magnetometer bandwidth is set by the optical pumping and relaxation rate R, which includes contributions from absorption of pumping and probing light and from spin relaxation processes in the cell. The optimal sensitivity is achieved when the laser absorption rates are comparable to the intrinsic spin-relaxation rates. However, a higher bandwidth is obtained by increasing the optical pumping rate beyond this optimal point without a great loss in sensitivity. Operation of the magnetometer with the bandwidth set to about 20 Hz has been carried out. This was improved, at a good signal/noise ratio upon operation at bandwidths up to 150 Hz. Thus, for MEG the bandwidth is increased to reduce the distortions of the magnetic signals, although the distortion could also be corrected using digital filters.

The bandwidth is easily increased to 100 Hz by increasing the optical pumping rate. In an MEG magnetometer, sensitivity is enhanced by increasing the density of K atoms slightly since a higher spin-relaxation rate can be tolerated. For this purpose the sensing cell is maintained at 200° C. to achieve density of about $1.5 \times 10^{14}$ cm$^3$ compared with previously used density of $6 \times 10^{13}$ cm$^3$.

In those improvements of an atomic magnetometer in which Johnson noise is eliminated, simple averaging of the existing channels is predicted to yield a sensitivity on the order of 0.2 fT/Hz$^{1/2}$. With optimization of additional operating parameters, such as an increase of the probe laser power and of the density of potassium atoms, one can approach a shot-noise-limited sensitivity predicted to be in the range $10^{-2}$–$10^{-3}$ fT/Hz$^{1/2}$ (see Example 2). The thermal magnetic noise produced by the brain (Varpula, T., et al, *J. Appl. Phys.* 55, 4015–4021 (1984)). is on the order of 0.1 fT/Hz$^{1/2}$, so an optimized embodiment of the magnetometer of the present invention will allow one to obtain the maximum possible amount of information about brain electrical activity. This may enable non-invasive studies of individual cortical modules in the brain (Ts'o, D. Y. et al., *Science* 249, 417–420 (1990)), which have a size of 0. 1–0.2 mm.

Example 8

Simultaneous Measurement of the Three Components of the Magnetic Field in Human Magnetoencephalography The human MEG magnetometer described in Example 6 is capable of measuring simultaneously the three orthogonal components of the magnetic field. Using two orthogonal probe lasers, both perpendicular to the pump beam, it is possible to simultaneously and independently measure 2 components of the magnetic field. Furthermore, although not wishing to be bound by theory, it is believed that the dependence of the signal on the $B_x$ and $B_z$ field components permits multidimensional measurement. If a small AC modulation at a first frequency is applied to $B_x$ field, the response of the magnetometer at that frequency is proportional to $B_z$ field. Conversely, a modulation of the $B_z$ field at the same or a second frequency gives a signal proportional to the $B_x$ field. A near-DC response of the magnetometer is still proportional to $B_y$. In a proof demonstrating this capability, the first and second modulations were applied at different frequencies at the same time. It was found that the magnetometer successfully measured simultaneously all 3 components of the magnetic field with just a single detector using appropriate frequency-dependent signal resolution.

Using this capability a 3-D map of all 3 components of the magnetic field with femtotesla sensitivity and a spatial resolution of several mm is obtained. In this way it is believed that the imaging capabilities of the human MEG magnetometer can approach that of magnetic resonance imaging (MRI).

Example 9

Spatial Resolution of Magnetic Field Sources

Figure 13:
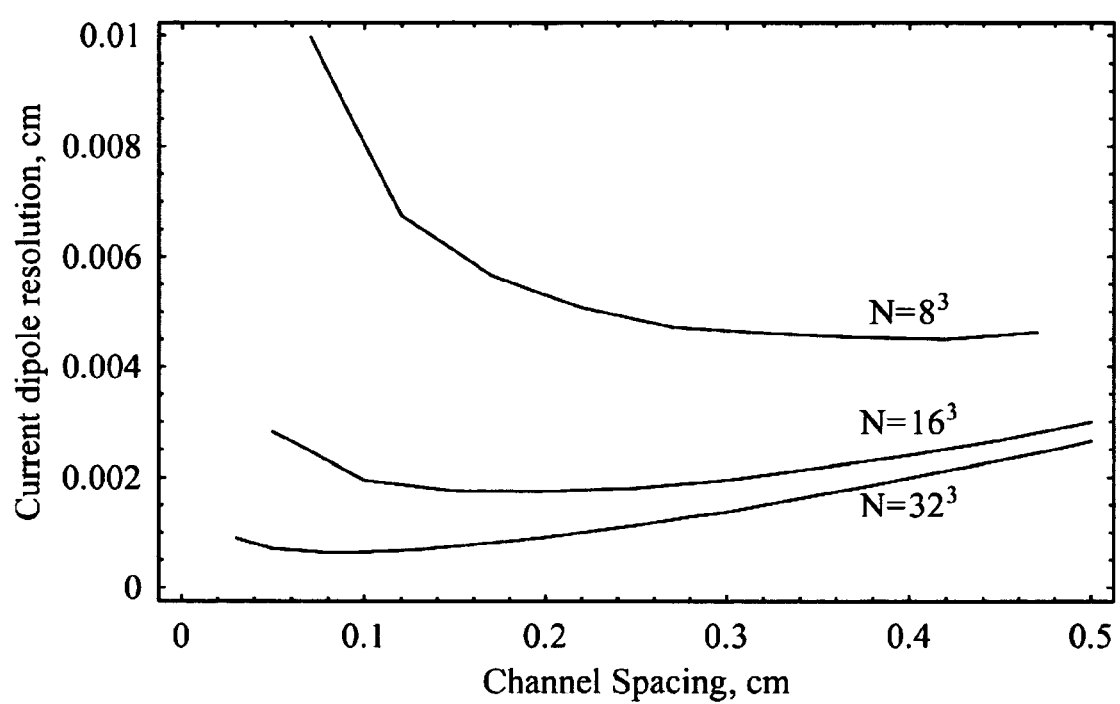
FIG. 13: Simulated localization accuracy of a single current dipole for a 3-D grid of measurement points as a function of the grid spacing and the number of measurement points.

The accuracy of source localization was modeled using a simple current dipole source. It was supposed that a current dipole to be measured in human MEG is located 2 cm below the surface of the head and that the edge of sensing cell begins 1 cm above the surface and is centered directly over the current dipole. A current dipole that produces a maximum field of 100 fT 1 cm above the surface of the head was employed. It was assumed that component of the magnetic field normal to the head is measured on a cubic 3-D array with 8 to 32 points on each side with an r.m.s. error of 1 fT. FIG. 13 shows the r.m.s. uncertainty in the position of the current dipole determined from a non-linear fit as a function of the number of measurement points and the grid spacing.

As expected, for a larger number of measurement points the optimal grid spacing is predicted to be smaller. Diffusion limits the spatial resolution inside the magnetometer to about 0.2 cm. This spacing between adjacent channels gives near-optimal resolution of 0.02 mm for $16^3$ measurement points.

For comparison, the same simulation for a typical SQUID arrangement was carried out, using about 250 magnetometers arranged around the surface of the head with inter-channel spacing of 2 cm. Assuming magnetic field noise of 5 fT rms, typical for commercial SQUID systems, localization resolution of 2 mm was obtained, in agreement with other similar simulations. Thus, an atomic magnetometer of the present invention provides a predicted improvement by a factor of 100 in localization accuracy over SQUID magnetometers, due both to the higher sensitivity and to the 3-dimentional arrangement of sensor points with small inter-channel spacing provided by the instant magnetometer.

Example 10

A multiple Sensing Cell Magnetometer Useful in Human MEG

A magnetometer useful in human diagnostic MEG is constructed having a plurality of sensing cells disposed at different locations about subject. This arrangement contributes to localizing sources of magnetic fields whose position within the subject is not known.

Testing of the Magnetometer

The magnetometer is initially tested with non-biological field sources. All magnetometer channels is individually calibrated using known external fields. The spatial localization performance of the magnetometer is first investigated using a small current loop that generates an easily calculable magnetic dipolar field. An MEG phantom using a saline-filled sphere is also constructed to simulate a current-dipole source in the brain. Various gradiometer configurations and non-linear fitting methods are to be tested to improve localization accuracy. After the localization performance has been established with non-biological sources, experiments with human volunteers will be performed.

First the somatosensory cortex will be mapped, where highly organized and well-localized sources of neural activity can be accurately and reliably activated under well-controlled experimental conditions. A non-magnetic tactile stimulator is constructed using a Braille cell. Stimulus triggering is synchronized with data acquisition and pump beam scanning across the cell.

A subject is initially examined with functional magnetic resonance imaging to determine the regions of their brain that become active under particular type of stimulation. For MEG imaging the measurement cell is positioned directly above the active brain regions. The exact orientation of a subject's head is measured using small calibration coils attached to their head.

Many parameters of the magnetometer are flexible and can be modified by a skilled artisan from measurements on human subjects. Parameters that are routinely examined include, by way of nonlimiting example, orientation of the lasers relative to the head, the size of the probe beam pixels, the size of the pump beam, the pumping rate, and the like. It is expected that this instrument will exceed in performance commercial MEG systems currently known in the field.

We claim:

1. A high sensitivity atomic magnetometer comprising:
   a) a sensing cell containing a mixture comprising an alkali metal vapor and a buffer gas, wherein the sensing cell is exposed to a background magnetic field lower than a predetermined value;
   b) means for increasing the magnetic polarization of the alkali metal vapor thereby increasing the sensitivity of the alkali metal vapor to a low intensity magnetic field;
   c) magnetizing means for imposing a magnetic field on a volume of space comprising the sensing cell;
   d) means for probing the magnetic polarization of the alkali metal vapor, the probing means providing an output from the alkali metal vapor, the output comprising characteristics related to the low intensity magnetic field; and
   e) measuring means wherein the measuring means receives the output, determines the characteristics of the low intensity magnetic field, and provides a representation of the low intensity magnetic field;
   wherein the limit of detectability of the atomic magnetometer is about 10 femtotesla $(Hz)^{-1/2}$.

2. The atomic magnetometer described in claim 1 further comprising magnetic shielding enclosing a region of space comprising the magnetizing means and the sensing cell.

3. The atomic magnetometer described in claim 1 wherein the predetermined value is about $10^{-8}$ tesla.

4. The atomic magnetometer described in claim 1 wherein the density of the alkali metal in the vapor is about $10^{11}$ cm$^{-3}$ or greater.

5. The atomic magnetometer described in claim 1 wherein the alkali metal is chosen from the group consisting of sodium, potassium, rubidium and cesium.

6. The atomic magnetometer described in claim 1 wherein the alkali metal is potassium.

7. The atomic magnetometer described in claim 1 wherein the buffer gas comprises a noble gas.

8. The atomic magnetometer described in claim 1 wherein the buffer gas comprises one or more isotopes of helium.

9. The atomic magnetometer described in claim 1 wherein the pressure of the buffer gas is in the range from about 1 atm to about 10 atm.

10. The atomic magnetometer described in claim 1 wherein the buffer gas further comprises nitrogen gas.

11. The atomic magnetometer described in claim 1 wherein the sensing cell is maintained at a temperature effective to provide an alkali metal vapor at a density greater than about $10^{11}$ cm$^{-3}$.

12. The atomic magnetometer described in claim 1 wherein the volume of the sensing cell is less than about 200 cm$^3$.

13. The atomic magnetometer described in claim 1 wherein the means for increasing the magnetic polarization of the alkali metal vapor comprises a first radiation generating means that generates a first beam of radiation illuminating the alkali metal vapor, the first beam being effective to increase the magnetic polarization of the alkali metal vapor.

14. The atomic magnetometer described in claim 13 wherein the first radiation generating means comprises a first laser device.

15. The atomic magnetometer described in claim 13 wherein the first radiation generating means further comprises a first optical polarizing means that polarizes the first beam of radiation.

16. The atomic magnetometer described in claim 13 wherein the first radiation generating means comprises a first optical polarizing means that imposes linear polarization on the first beam of radiation.

17. The atomic magnetometer described in claim 13 wherein the first radiation generating means comprises a first optical polarizing means that imposes circular polarization on the first beam of radiation.

18. The atomic magnetometer described in claim 13 wherein the first radiation generating means further comprises a first modulator that modulates the first beam of radiation by a first modulation function.

19. The atomic magnetometer described in claim 1 wherein the probing means comprises a second radiation generating means that generates a second beam of radiation traversing the alkali metal vapor and wherein the output comprises the second beam after it traverses the vapor.

20. The atomic magnetometer described in claim 19 wherein the second radiation generating means comprises a second laser device.

21. The atomic magnetometer described in claim 19 wherein the second radiation generating means further comprises a second optical polarizing means that polarizes the second beam of radiation.

22. The atomic magnetometer described in claim 21 wherein the second radiation generating means comprises a second optical polarizing means that imposes linear polarization on the second beam of radiation.

23. The atomic magnetometer described in claim 21 wherein the second radiation generating means comprises a second optical polarizing means that imposes circular polarization on the second beam of radiation.

24. The atomic magnetometer described in claim 19 wherein the second radiation generating means comprises a second modulator that modulates the second beam of radiation by a second modulation function.

25. The atomic magnetometer described in claim 1 wherein the magnetizing means provides a probing magnetic field in one, two, or all three of the orthogonal directions, x, y, and/or z.

26. The atomic magnetometer described in claim 1 wherein the magnetizing means provides a probing magnetic field modulated by a third modulation function.

27. The atomic magnetometer described in claim 1 wherein the measuring means comprises an output detecting means that provides a signal comprising characteristics related to the low intensity magnetic field, and a signal processing means for receiving the signal and providing the representation.

28. The atomic magnetometer described in claim 27 wherein the output detecting means comprises radiation detecting means that detects a second beam of radiation output from the alkali metal vapor.

29. The atomic magnetometer described in claim 28 further comprising a third optical polarizing means placed between the sensing cell and the radiation detecting means.

30. The atomic magnetometer described in claim 29 wherein the third optical polarizing means comprises a linear polarization analyzer.

31. The atomic magnetometer described in claim 29 wherein the third optical polarizing means comprises a circular polarization analyzer.

32. The atomic magnetometer described in claim 28 wherein the radiation detecting means comprises a photodetector, wherein the photodetector provides a signal comprising characteristics related to the low intensity magnetic field.

33. The atomic magnetometer described in claim 32 wherein the signal comprises a component modulated by a first modulation function or a second modulation function, or both.

34. The atomic magnetometer described in claim 27 wherein the signal processing means receives at least a portion of a signal from the output detecting means, wherein the signal processing means resolves characteristics related to the low intensity magnetic field from the signal and provides a representation thereof, the representation characterizing the low intensity magnetic field detected by the sensing cell.

35. The atomic magnetometer described in claim 34 wherein the signal is modulated by a first modulation function or a second modulation function, or both, wherein the signal processing means detects a component in the signal that is modulated by the first modulation function or the second modulation function, or both.

36. A method for providing a representation of a low intensity magnetic field detected by a sensing cell that has high sensitivity to a magnetic field, the method comprising the steps of:
   a) providing an atomic magnetometer described in claim 1;
   b) increasing the magnetic polarization of the alkali metal vapor, thereby increasing the sensitivity of the alkali metal vapor to a low intensity magnetic field;
   c) reorienting the magnetic polarization of the alkali metal vapor using a magnetic field;
   d) probing the magnetic polarization of the reoriented alkali metal vapor with the probing means, wherein the probing means provides an output whose characteristics are related to the low intensity magnetic field; and
   e) receiving the output in the measuring means, determining the characteristics of the low intensity magnetic field, and providing a representation of the low intensity magnetic field detected by the sensing cell.

37. The method described in claim 36 wherein the density of the alkali metal in the vapor is about $10^{11}$ cm$^{-3}$ or greater.

38. The method described in claim 36 wherein the atomic magnetometer further comprises magnetic shielding enclosing a region of space comprising the sensing cell.

39. The method described in claim 36 wherein the alkali metal is chosen from the group consisting of sodium, potassium, rubidium and cesium.

40. The method described in claim 36 wherein the buffer gas comprises a noble gas.

41. The method described in claim 36 wherein the pressure of the buffer gas is in the range from about 1 atm to about 10 atm.

42. The method described in claim 36 wherein the sensing cell transmits a plurality of beams of radiation through the alkali metal vapor, wherein at least two of the beams are physically resolved from each other.

43. The method described in claim 36 wherein the means for increasing the magnetic polarization of the alkali metal vapor comprises a first radiation generating means that generates a first beam of radiation illuminating the alkali metal vapor, the first beam being effective to increase the magnetic polarization of the alkali metal vapor.

44. The method described in claim 36 wherein the probing means comprises a second radiation generating means that generates a second beam of radiation traversing the alkali metal vapor and wherein the output comprises the second beam after it traverses the vapor.

45. The atomic magnetometer described in claim 36 wherein the magnetizing means provides a probing magnetic field in one, two, or all three of the orthogonal directions, x, y, and/or z.

46. The method described in claim 36 wherein the measuring means comprises an output detecting means that provides a signal comprising characteristics related to the low intensity magnetic field, and a signal processing means for receiving the signal and providing the representation.

47. A high sensitivity atomic magnetometer that generates a representation of a first magnetic field originating within a sample volume, the magnetometer comprising:
   a) a sensing cell sensitive to low intensity magnetic fields comprising an alkali metal vapor and a buffer gas, the sensing cell being adjacent to a sample volume including a component generating a first magnetic field, wherein the sensing cell is exposed to a background magnetic field lower than a predetermined value;
   b) means for increasing the magnetic polarization of the alkali metal vapor, wherein the magnetic polarization of the alkali metal vapor includes a contribution from the first magnetic field;
   c) magnetizing means for imposing a magnetic field on a volume of space comprising the sensing cell;
   d) means for probing the magnetic polarization of the alkali metal vapor, the probing means providing an output from the vapor comprising characteristics related to the first magnetic field; and
   e) measuring means for receiving the output, determining the characteristics of the first magnetic field, and providing a representation of the first magnetic field;
   wherein the limit of detectability of the atomic magnetometer is about 10 femtotesla (Hz)$^{-1/2}$.

48. The atomic magnetometer described in claim 47 wherein the sample volume comprises at least a portion of a mammalian subject.

49. The atomic magnetometer described in claim 47 further comprising magnetic shielding enclosing a region of space comprising the magnetizing means, the sample volume and the sensing cell.

50. The atomic magnetometer described in claim 47 wherein the predetermined value is about $10^{-8}$ tesla.

51. The atomic magnetometer described in claim 47 wherein the density of the alkali metal in the vapor is about $10^{11}$ cm$^{-3}$ or greater.

52. The atomic magnetometer described in claim 47 wherein the alkali metal is chosen from the group consisting of sodium, potassium, rubidium and cesium.

53. The atomic magnetometer described in claim 47 wherein the buffer gas comprises a noble gas.

54. The atomic magnetometer described in claim 47 wherein the pressure of the buffer gas is in the range from about 1 atm to about 10 atm.

55. The atomic magnetometer described in claim 47 wherein the means for increasing the magnetic polarization of the alkali metal vapor comprises a first radiation generating means that generates a first beam of radiation illuminating the alkali metal vapor, the first beam being effective to increase the magnetic polarization of the alkali metal vapor.

56. The atomic magnetometer described in claim 47 wherein the probing means comprises a second radiation generating means that generates a second beam of radiation traversing the alkali metal vapor and wherein the output comprises the second beam after it traverses the vapor.

57. The atomic magnetometer described in claim 47 wherein the measuring means comprises an output detecting means that provides a signal comprising characteristics related to the low intensity magnetic field, and a signal processing means for receiving the signal and providing the representation.

58. A method for providing a representation of a first magnetic field originating within a sample volume, the method comprising the steps of:
   a) providing a high sensitivity apparatus described in claim 47;
   b) identifying a sample volume adjacent to the sensing cell;
   c) increasing the magnetic polarization of the alkali metal vapor, wherein the magnetic polarization of the alkali metal vapor includes a contribution from the first magnetic field;
   d) reorienting the magnetic polarization of the alkali metal vapor using a magnetic field;
   e) probing the magnetic polarization of the reoriented alkali metal vapor with the probing means, wherein the probing means provides an output whose characteristics are related to the first magnetic field; and
   f) receiving the output in the measuring means, wherein the measuring means determines the characteristics of the first magnetic field and provides a representation of the first magnetic field detected by the sensing cell.

59. The method described in claim 58 wherein the sample volume comprises at least a portion of a mammalian subject.

60. The method described in claim 58 wherein the density of the alkali metal in the vapor is about $10^{11}$ cm$^{-3}$ or greater.

61. The method described in claim 58 wherein the high sensitivity apparatus further comprises magnetic shielding enclosing a region of space comprising the sample volume and the sensing cell.

62. The method described in claim 58 wherein the predetermined value is about $10^{-8}$ tesla.

63. The method described in claim 58 wherein the alkali metal is chosen from the group consisting of sodium, potassium, rubidium and cesium.

64. The method described in claim 58 wherein the buffer gas comprises a noble gas.

65. The method described in claim 58 wherein the pressure of the buffer gas is in the range from about 1 atm to about 10 atm.

66. The method described in claim 58 wherein the means for increasing the magnetic polarization of the alkali metal vapor comprises a first radiation generating means that generates a first beam of radiation illuminating the alkali metal vapor, the first beam being effective to increase the magnetic polarization of the alkali metal vapor.

67. The method described in claim 58 wherein the probing means comprises a second radiation generating means that generates a second beam of radiation traversing the alkali metal vapor and wherein the output comprises the second beam after they traverse it traverses the vapor.

68. The method described in claim 58 wherein the measuring means comprises an output detecting means that provides a signal comprising characteristics related to the low intensity magnetic field, and a signal processing means for receiving the signal and providing the representation.

69. The method described in claim 58 wherein the representation comprises a representation of a source of a first magnetic field occurring within the sample volume displayed in one of three orthogonal Cartesian coordinates referenced to the sample volume.

70. The method described in claim 58 wherein the representation comprises a representation of a source of a first magnetic field occurring within the sample volume displayed in two of three orthogonal Cartesian coordinates referenced to the sample volume.

71. The method described in claim 58 wherein the representation comprises a representation of a source of a first magnetic field occurring within the sample volume displayed in three of three orthogonal Cartesian coordinates referenced to the sample volume.

72. A high sensitivity diagnostic imaging atomic magnetometer comprising:
   a) a sensing cell sensitive to low intensity magnetic fields, the sensing cell comprising an alkali metal vapor and a buffer gas, the sensing cell being adjacent to a sample volume for containing at least a portion of a subject that generates a first magnetic field, wherein the sensing cell is exposed to
      i) the first magnetic field; and
      ii) a background magnetic field;
   b) a first radiation generating means that generates a first beam of radiation illuminating the alkali metal vapor, the first beam being effective to increase the magnetic polarization of the alkali metal vapor, wherein the magnetic polarization of the alkali metal vapor includes a contribution from the first magnetic field;
   c) magnetizing means for imposing a second magnetic field on a volume of space comprising the sensing cell;
   d) a second radiation generating means that generates a second beam of radiation traversing the alkali metal vapor for probing the magnetic polarization of the alkali metal vapor, the second radiation beam providing a second output beam of radiation after it traverses the vapor, the second output beam comprising characteristics related to the first magnetic field;
   e) output detecting means that detects the second output beam and provides a signal comprising characteristics related to the first magnetic field; and
   f) a computational module comprising a signal processing means for
      i) receiving the signal;
      ii) determining the characteristics of the first magnetic field present in the signal; and
      iii) providing a representation of the first magnetic field;
wherein the representation is useful in diagnostic imaging of the subject.

73. A method of conducting diagnostic imaging on a subject comprising the steps of:
   a) placing at least a portion of the subject that generates a first magnetic field in a sample volume adjacent to a sensing cell sensitive to low intensity magnetic fields, the sensing cell comprising an alkali metal vapor and a buffer gas, wherein the sensing cell is exposed to
      i) the first magnetic field; and
      ii) a background magnetic field;
   b) increasing the magnetic polarization of the alkali metal vapor by illuminating the alkali metal vapor with a first beam of radiation, wherein the magnetic polarization of the alkali metal vapor includes a contribution from the first magnetic field;
   c) reorienting the magnetic polarization of the alkali metal vapor by imposing a second magnetic field on a volume of space comprising the sensing cell;
   d) probing the magnetic polarization of the alkali metal vapor with a second beam of radiation that traverses the alkali metal vapor, the second radiation beam providing a second output beam of radiation after it traverses the vapor, the second output beam comprising characteristics related to the first magnetic field;
e) detecting the second output beam with an output detecting means that provides a signal comprising characteristics related to the first magnetic field; and
f) receiving the signal in a computational module comprising a signal processing means that i) determines the characteristics of the first magnetic field present in the second output signal; and
ii) provides a representation of the first magnetic field; wherein the representation is useful in diagnostic imaging of the subject.

* * * * *

UNITED STATES PATENT AND TRADEMARK OFFICE
CERTIFICATE OF CORRECTION

PATENT NO. : 7,145,333 B2  
APPLICATION NO. : 11/135853  
DATED : December 5, 2006  
INVENTOR(S) : Michael Romalis et al.

It is certified that error appears in the above-identified patent and that said Letters Patent is hereby corrected as shown below:

Column 1, line 48, "$Hz^{12}$" should be replaced with --$Hz^{1/2}$.--

Column 4, line 2, the word "described" should be deleted as it is written twice.

Column 16, line 14, "$(Hz)^{-12}$" should be replaced with --$(Hz)^{-1/2}$.--

Column 19, line 36, "$f_{mod}=2.9$" should be replaced with --$f_{mod}=2.9$.--

Column 20, line 14, "$\Delta Am=1$" should be replaced with --$\Delta m=1$.--

Column 24, line 22 "$\alpha m_m^2$" should be replaced with --$\alpha^2_m$.--

Column 24, lines 30 and 38, "$1/f$" should be replaced with --$1/f$.--

Signed and Sealed this

First Day of May, 2007

JON W. DUDAS  
*Director of the United States Patent and Trademark Office*